(12) United States Patent
Han

(10) Patent No.: US 10,751,548 B2
(45) Date of Patent: Aug. 25, 2020

(54) AUTOMATED IMAGE SEGMENTATION USING DCNN SUCH AS FOR RADIATION THERAPY

(71) Applicant: Elekta, Inc., Atlanta, GA (US)

(72) Inventor: Xiao Han, Chesterfield, MO (US)

(73) Assignee: Elekta, Inc., Atlanta, GA (US)

( * ) Notice: Subject to any disclaimer, the term of this patent is extended or adjusted under 35 U.S.C. 154(b) by 240 days.

(21) Appl. No.: 15/896,548

(22) Filed: Feb. 14, 2018

(65) Prior Publication Data

US 2019/0030371 A1 Jan. 31, 2019

Related U.S. Application Data

(60) Provisional application No. 62/538,160, filed on Jul. 28, 2017.

(51) Int. Cl.
*A61N 5/10* (2006.01)
*G06T 17/20* (2006.01)
(Continued)

(52) U.S. Cl.
CPC ........... *A61N 5/1039* (2013.01); *A61N 5/103* (2013.01); *G06K 9/3233* (2013.01);
(Continued)

(58) Field of Classification Search
CPC ........ A61N 5/1039; A61N 5/103; G06T 7/11; G16H 50/20; G16H 30/40; G06K 9/3233; G06K 9/66; G06N 3/0454; G06N 3/08
See application file for complete search history.

(56) References Cited

U.S. PATENT DOCUMENTS 9,589,374 B1 * 3/2017 Gao ...................... G06T 7/0012
9,968,257 B1 * 5/2018 Burt ..................... A61B 5/7267
(Continued)

OTHER PUBLICATIONS

"International Application Serial No. PCT/US2017/048245, International Search Report and Written Opinion dated Oct. 10, 2017", 14 pgs.
(Continued)

*Primary Examiner* — Santiago Garcia
(74) *Attorney, Agent, or Firm* — Schwegman Lundberg & Woessner, P.A.; Sanjay Agrawal

(57) ABSTRACT

Features, such as anatomical features, may be automatically segmented from medical imaging information, using a computer-implemented method. In an example, three-dimensional (3D) medical imaging information may be received, such as defining a first volume. A first trained convolutional neural network (CNN) may be applied to the three-dimensional medical imaging information. An output from the first trained CNN may be used to determine a region-of-interest within the first volume, the region-of-interest defining a lesser, second volume. A different, second trained CNN may be applied to the region-of-interest, a segmented representation of the 3D medical imaging information may be provided using the outputs from the first and second CNNs, where the second CNN provides enhanced segmentation detail in the region-of-interest without requiring application of the second CNN to an entirety of the first volume. Techniques are also described from training one or more of the first and second CNNs.

22 Claims, 10 Drawing Sheets

(51) Int. Cl.
| | |
|---|---|
| *G06T 7/00* | (2017.01) |
| *G06K 9/66* | (2006.01) |
| *G06T 7/11* | (2017.01) |
| *G16H 30/40* | (2018.01) |
| *G16H 50/20* | (2018.01) |
| *G06N 3/08* | (2006.01) |
| *G06K 9/32* | (2006.01) |
| *G06K 9/62* | (2006.01) |
| *G06N 3/04* | (2006.01) |
| *A61B 90/00* | (2016.01) |
| *G16H 20/40* | (2018.01) |

(52) U.S. Cl.
CPC ............ *G06K 9/6282* (2013.01); *G06K 9/66* (2013.01); *G06N 3/0454* (2013.01); *G06N 3/08* (2013.01); *G06T 7/0012* (2013.01); *G06T 7/11* (2017.01); *G06T 17/20* (2013.01); *G16H 30/40* (2018.01); *G16H 50/20* (2018.01); *A61B 2090/374* (2016.02); *A61B 2090/378* (2016.02); *A61B 2090/3762* (2016.02); *G06T 2207/10072* (2013.01); *G06T 2207/10081* (2013.01); *G06T 2207/10088* (2013.01); *G06T 2207/20081* (2013.01); *G06T 2207/20084* (2013.01); *G06T 2207/30081* (2013.01); *G16H 20/40* (2018.01)

(56) References Cited

U.S. PATENT DOCUMENTS

| | | | | |
|---|---|---|---|---|
| 10,366,494 | B2* | 7/2019 | Seong | G06K 9/6267 |
| 10,496,899 | B1* | 12/2019 | Kim | G06K 9/6256 |
| 2005/0251021 | A1* | 11/2005 | Kaufman | A61B 5/411 600/407 |
| 2017/0161891 | A1* | 6/2017 | Madabhushi | G06T 7/0012 |
| 2017/0301095 | A1* | 10/2017 | Zhang | G06T 7/12 |
| 2018/0108139 | A1* | 4/2018 | Abramoff | G06T 7/11 |
| 2018/0285715 | A1* | 10/2018 | Son | G06N 3/08 |
| 2018/0349724 | A1* | 12/2018 | Xiang | G06K 9/3233 |
| 2019/0050999 | A1* | 2/2019 | Piat | G06T 7/33 |
| 2019/0188541 | A1* | 6/2019 | Wang | G01C 3/08 |

OTHER PUBLICATIONS

"International Application Serial No. PCT/US2017/048271, International Search Report dated Nov. 28, 2017", 5 pgs.

"International Application Serial No. PCT/US2017/048271, Written Opiniont dated Nov. 28, 2017", 12 pgs.

Chen, Hao, et al., "Automatic Localization and Identification of Vertebrae in Spine CT via a Joint Learning Model with Deep Neural Networks", Medical Image Computing and Computer-Assisted Intervention—MICCAI 2015, LNCS 9349, (2015), 515-522.

Chevrefils, Claudia, et al., "Quantitative evaluation of an automatic segmentation method for 3D reconstruction of intervertebral scoliotic disks from MR images", BMC Medical Imaging, 12(1), (2012), 14 pgs.

Cicek, Ozgun, et al., "3D U-Net: Learning Dense Volumetric Segmentation from Sparse Annotation", (Jun. 21, 2016), 8 pgs.

Erickson, Bradley J., et al., "Deep Learning in Radiology: Does One Size Fit All?", Journal of the American College of Radiology, Feb. 2018, vol. 15, No. 2, (Feb. 3, 2018), 6 pgs.

Han, Xiao, "Automatic Liver Lesion Segmentation Using a Deep Convolutional Neural Network Method", Elekta, (Apr. 2017), 4 pgs.

Han, Xiao, "MR-based synthetic CT generation using a deep convolutional neural network MR-based synthetic CT generation using a deep convolutional neural network method", Med Phys 44 (4), (Mar. 21, 2017), 1408-1420.

Lai, Matthew, "Deep Learning for Medical Image Segmenttion", [online]. Retrieved from the Internet: <URL: https://arxiv.org/pdf/1505.02000v1.pdf?, (2015), 1-23.

Setio, Arnaud A. A., et al., "Pulmonary Nodule Detection in CT Images: False Positive Reduction Using Multi-View Convolutional Networks", IEEE Transactions on Medical Imaging, 35(5), (May 2016), 1160-1169.

Shin, Hoo-Chang, et al., "Deep Convolutional Neural Networks for Computer-Aided Detection: CNN Architectures, Dataset Characteristics and Transfer Learning", IEEE Transactions on Medical Imaging, 35(5), (May 2016), 1285-1298.

* cited by examiner

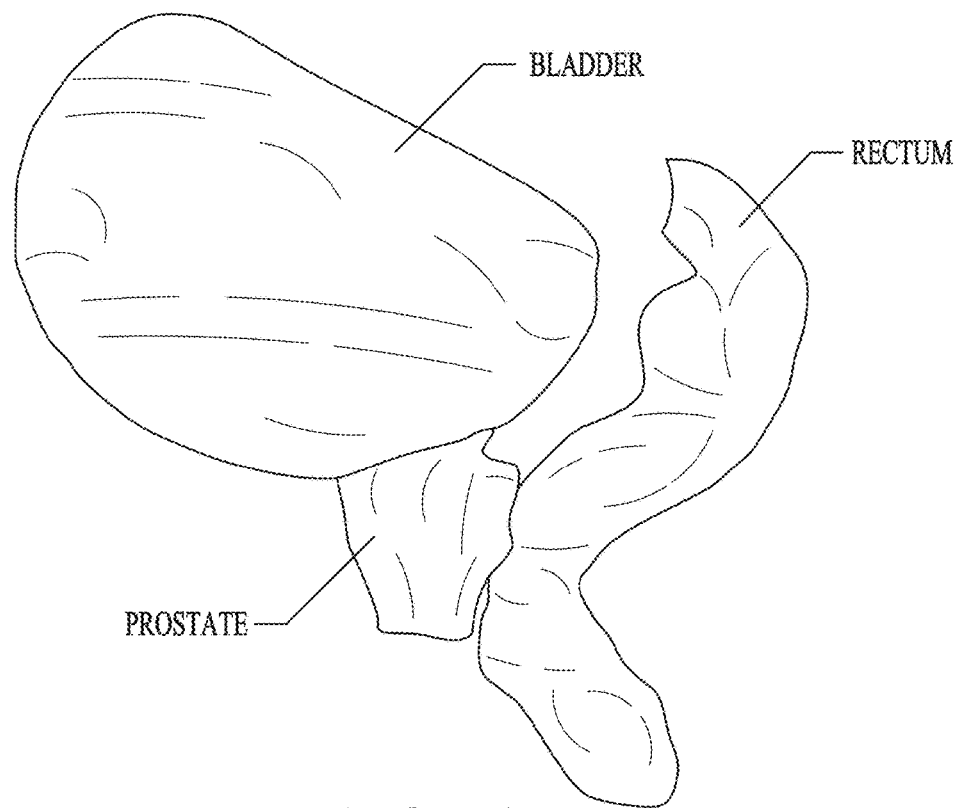
*FIG. 1A*
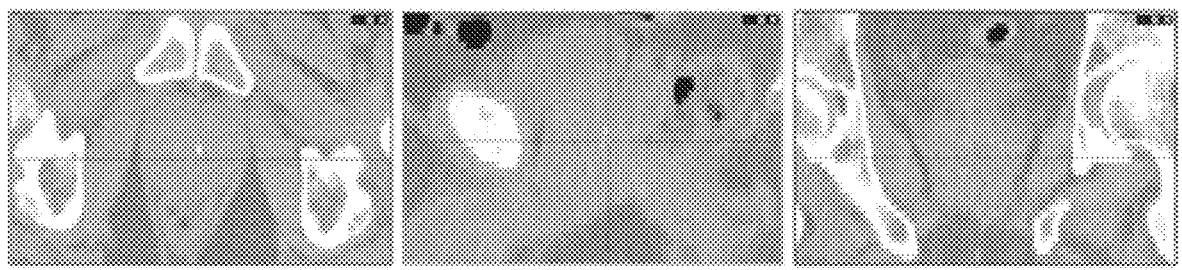
*FIG. 1B*  *FIG. 1C*  *FIG. 1D*
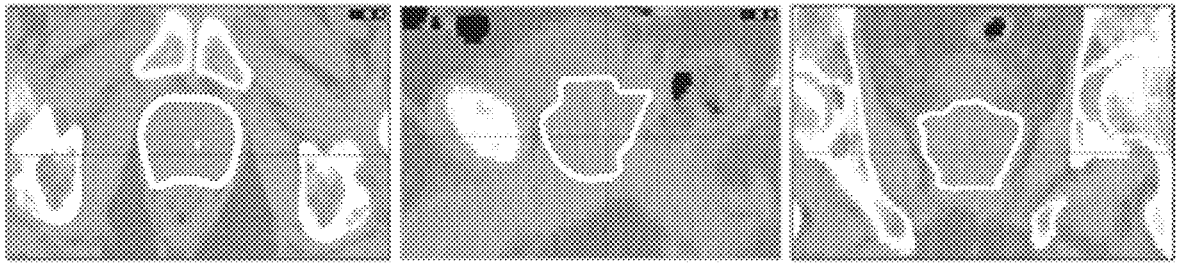
*FIG. 1E*  *FIG. 1F*  *FIG. 1G*

AUTOMATED IMAGE SEGMENTATION USING DCNN SUCH AS FOR RADIATION THERAPY

CLAIM OF PRIORITY

This patent application claims the benefit of priority of Han, U.S. Provisional Patent Application Ser. No. 62/538,160, titled "AUTOMATIC IMAGE SEGMENTATION USING DEEP CONVOLUTIONAL NEURAL NETWORKS," filed on Jul. 28, 2017, which is hereby incorporated by reference herein in its entirety.

TECHNICAL FIELD

This document pertains generally, but not by way of limitation, to segmentation of medical images, and more particularly, to use of automated image segmentation using a neural network, such as in support of radiation therapy delivery or radiation therapy treatment planning.

BACKGROUND

In radiotherapy or radiosurgery, treatment planning is generally performed using medical imaging of the patient. Analysis of such imaging generally involves delineation of target volumes and critical organs in the medical images. For example, segmentation or contouring of tumor and organs-at-risk (OARs) from patient images is generally considered a prerequisite for radiotherapy planning. Manual segmentation is generally tedious, time-consuming, and may suffer from large intra-rater and inter-rater variations. Fully automated segmentation of x-ray computed tomography (CT) or magnetic resonance (MR) images using generally-available techniques has been proven to be challenging, such as due to image noise or other artifacts. Such imaging generally provides only limited image contrast for most soft-tissue structures, in one approach, atlas-based auto-segmentation (ABAS) techniques may be used, and provide an ability to incorporate prior anatomical information about structure shapes and their geometric relationships. ABAS-based approaches may present challenges. For example, in ABAS, segmentation accuracy generally depends on atlas quality, and a computation time is generally proportional to a count of atlases used. In an example, a multi-atlas label fusion technique, may be used, but segmentation accuracy may be unsatisfactory for certain applications and manual editing of the results may still be performed.

OVERVIEW

As mentioned above, structure segmentation from patient CT or MR images is generally a prerequisite for radiotherapy planning. Online adaptive radiotherapy planning may be defined as involving accurate and fast automatic image segmentation. Deep learning (DL), such as involving use of deep convolutional neural networks (DCNN) may be used as an efficient automated image segmentation technique. The present inventor has developed, among other things, a multi-model DCNN scheme to provide automatic segmentation of 3D medical images with better computational efficiency as compared to other approaches, such as compared particularly to an atlas-based auto-segmentation (ABAS) technique. In an example, a two-dimensional (2D) or 2.5D technique may include a first DCNN model trained and deployed to segment large structures (such as the skin surface and the lungs) in an image. In a 2.5D approach, 2D slices (such as adjacent slices) are partitioned from 3D input data and analyzed. Such a 2D or 2.5D technique may produce a quick estimation of small or thin, elongated structures such as the esophagus and the spinal cord. A second DCNN model (e.g., a DCNN capable of processing 3D imaging information without requiring the inputs to be decomposed into 2D representations) may be trained to get more accurate segmentation of such small or thin and elongated structures.

Directly applying a 3D DCNN model to process a full 3D image data set may produce an undesirably long segmentation duration (when such an approach is even computationally feasible). By contrast, the present inventor has recognized, among other things, that 2D (or 2.5D) model results may be used to automatically define a smaller region-of-interest, within which a separate 3D DCNN model may be applied more efficiently, because the 3D DCNN model need not be applied to the full 3D input volume in its entirety. In an example, 2D or 2.5D DCNN model results may also be used as extra input (besides the original image data) to the 3D DCNN model so that the 3D DCNN model may make refinement based on the initial segmentation by the 2D or 2.5D DCNN.

In an example, a computer-implemented method for segmentation of anatomical features from 3D medical imaging information may include receiving the three-dimensional (3D) medical imaging information defining a first volume, applying a first trained convolutional neural network (CNN) to the three-dimensional medical imaging information, using an output from the first trained CNN determine a region-of-interest within the first volume, the region-of-interest defining a lesser, second volume, applying a different, second trained CNN to the region-of-interest, and providing a segmented representation of the three-dimensional medical imaging information using the outputs from the first and second CNNs, wherein the second CNN provides enhanced segmentation detail in the region-of-interest without requiring application of the second CNN to an entirety of the first volume.

In an example, a computer-implemented method for establishing first and second convolutional neural network (CNN) models for segmentation of anatomical features from 3D medical imaging information may include receiving a set of training images and corresponding ground truth classification maps of anatomical features, using the set of training images and the corresponding ground truth classification maps to determine a gradient of a first loss function and distributing information indicative of an error provided by the calculated gradient back through a first CNN model to train the first CNN model, and using the set of training images and the corresponding classification maps to determine a gradient of a second loss function and distributing information indicative of an error provided by the calculated gradient back through a second CNN model to train the second CNN model. In an example, at least one of the first and second loss functions comprises a cross-entropy loss function, and the second CNN provides enhanced segmentation detail as compared to the first CNN when the first and second. CNNs are applied serially to the 3D medical imaging information.

A system for segmentation of anatomical features from 3D medical imaging information may include processing circuitry comprising at least one processor and a storage medium comprising instructions, which when executed by the at least one processor, cause the processor to receive the three-dimensional (3D) medical imaging information defining a first volume, apply a first trained convolutional neural network (CNN) to the three-dimensional medical imaging information, use an output from the first trained CNN to determine a region-of-interest within the first volume, the region-of-interest defining a lesser, second volume, apply a different, second trained CNN to the region-of-interest, and provide a segmented representation of the three-dimensional medical imaging information using the outputs from the first and second CNNs, wherein the second CNN provides enhanced segmentation detail in the region-of-interest without requiring application of the second CNN to an entirety of the first volume.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1A illustrates generally an illustrative example of a segmented three-dimensional (3D) computed tomography (CT) image from a pelvic region of a prostate cancer patient.

FIG. 1B, FIG. 1C, and FIG. 1D illustrate corresponding axial, sagittal, and coronal planes from a 3D CT image of the same pelvic region as depicted in FIG. 1A.

FIG. 1E, FIG. 1F, and FIG. 1G illustrate expected prostate contours overlaid on the views of FIG. 1B, FIG. 1C, and FIG. 1D, with such images illustrating that generally-available image segmentation techniques solely based on contrast or texture would likely fail in properly identifying the prostate contour.

DETAILED DESCRIPTION

Figure 2:
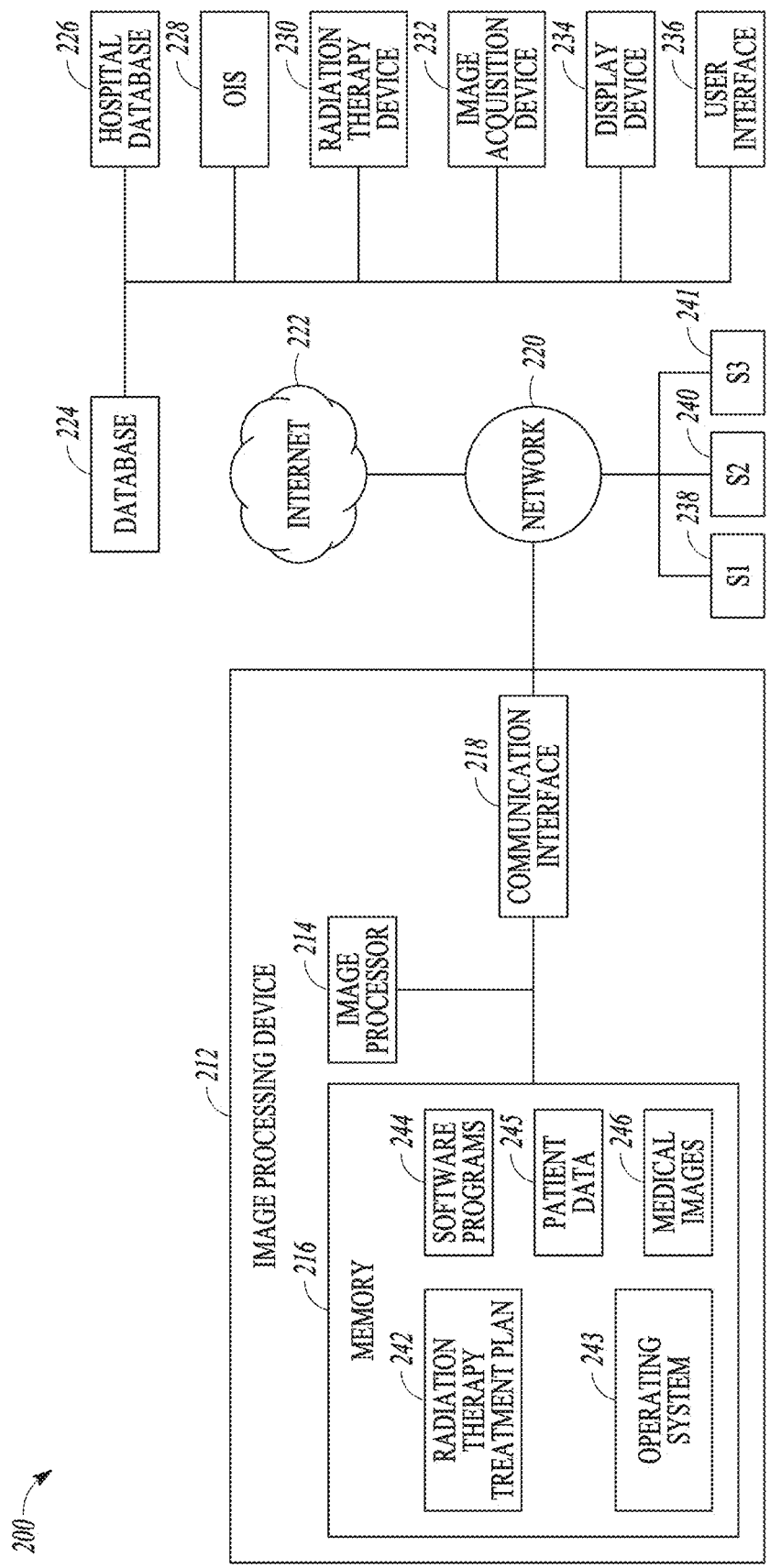
FIG. 2 illustrates an example comprising a radiotherapy system 100, such as for providing radiation therapy to a patient.

FIG. 1A illustrates generally an illustrative example of a segmented three-dimensional (3D) computed tomography (CT) image from a pelvic region of a prostate cancer patient. FIG. 1B, FIG. 1C, and FIG. 1D illustrate corresponding axial, sagittal, and coronal planes from a 3D CT image of the same pelvic region as depicted in FIG. 1A. A prostate boundary is generally not visible in FIG. 1B, FIG. 1C, and FIG. 1D, and the prostate contour may not generally be distinguished from other anatomical structures based on such images. FIG. 1E, FIG. 1F, and FIG. 1G illustrate expected prostate contours overlaid on the views of FIG. 1B, FIG. 1C, and FIG. 1D, with such images illustrating that generally-available image segmentation techniques solely based on contrast or texture would likely fail in properly identifying the prostate contour.

Various approaches may be used to perform automated or semi-automated segmentation of medical images. In one approach, an atlas-based auto-segmentation (ABAS) technique may be used. ABAS techniques generally involve mapping of contours in an image based on a previously-defined anatomy configuration obtained from a reference image. Such a reference image may serve as the "atlas." Generally, an accuracy of an ABAS technique depends on a performance of registration between the atlas and the new imaging information to be mapped. Shapes and sizes of some organs may vary for different patients, and may be deformed in large scales at different stages for the same patient. Such variation or distortion may decrease a registration accuracy and may thereby affect performance of ABAS techniques. Other approaches may be used. For example, recent developments in machine learning techniques may provide accurate segmentation of low-contrast parts in images or may perform such segmentation on lower quality images as compared to other approaches. For example, various machine learning techniques may involve "training" the machines, computers, or computer programs to predict (e.g., by estimating the likelihood of) each pixel or voxel of a medical image being associated with or otherwise representing a particular anatomical structure.

Such prediction or estimation may involve use of one or more features of the medical image as input. A performance of such an approach than thereby depend on the types of features available. For example, a Random Forest (RF) technique may be used for image segmentation. Such an RF model may be built based on extracting different features from a set of training samples. Generally, features employed in the RF method are still established manually and are specific for contouring one type of organ. Accordingly, such an RF technique may present disadvantages such as making it tedious or time-consuming to establish an optimal combination of features for different segmentation applications. Accordingly, the present inventors have recognized that other segmentation approaches such as involving convolutional neural networks (CNNs) may help to address such challenges.

In particular, deep learning techniques, including deep convolutional neural networks (DCNNs), may be used for challenging medical imaging analysis problems, such as tumor detection, disease classification, or structure segmentation, as illustrative examples. A property that contributes to the success of DCNNs is an ability for such DCNNs to discern or "learn" a complex model directly from raw input data, without relying on hand-crafted features. The techniques described herein may be used to provide DCNN-facilitated automatic-segmentation of CT or MR images, as illustrative examples. For example, according to illustrative examples herein, such techniques may be evaluated by using them to segment five OARs (e.g., the left and right lungs, the heart, the esophagus, and the spinal cord) from thoracic CT images of lung cancer patients. In particular, a two-model scheme may be used to obtain accurate segmentation results with high computational efficiency, as compared to other approaches.

FIG. 2 illustrates an example comprising a radiotherapy system 200, such as for providing radiation therapy to a patient. The radiotherapy system 200 includes an image processing device, 212. The image processing device 212 may be connected to a network 220. The network 220 may be connected to the Internet 222. The network 220 may connect the image processing device 212 with one or more of a database 224, a hospital database 226, an oncology information system (OIS) 228, a radiation therapy device 230, an image acquisition device 232, a display device 234, and a user interface 236. The image processing device 212 may be configured to generate radiation therapy treatment plans 242 to be used by the radiation therapy device 230.

The image processing device 212 may include a memory device 216, a processor 214 and a communication interface 218. The memory device 216 may store computer-executable instructions, such as an operating system 243, a radiation therapy treatment plans 242 (e.g., original treatment plans, adapted treatment plans and the like), software programs 244 (e.g., artificial intelligence, deep learning, neural networks, radiotherapy treatment plan software), and any other computer-executable instructions to be executed by the processor 214, such as corresponding to or using one or more techniques as shown and described elsewhere herein. In one embodiment, the software programs 244 may convert medical images of one format (e.g., MRI) to another format (e.g., CT) by producing synthetic images, such as a pseudo-CT image. For instance, the software programs 244 may include image processing programs to train a predictive model for converting a medial image 246 in one modality (e.g., an MRI image) into a synthetic image of a different modality (e.g., a pseudo CT image); alternatively, the trained predictive model may convert a CT image into an MRI image. In another embodiment, the software programs 244 may register the patient image (e.g., a CT image or an MR image) with that patient's dose distribution (also represented as an image) so that corresponding image voxels and dose voxels are associated appropriately by the network. In yet another embodiment, the software programs 244 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 244 may substitute functions of the dose distribution that emphasize some aspect of the dose information. Such functions might emphasize steep gradients around the target, or any other structural aspect useful to neural network learning. The memory device 216 may store data, including medical images 246, patient data 245, and other data required to create and implement a radiation therapy treatment plan 242.

In addition to the memory 216 storing the software programs 244, it is contemplated that software programs 244 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 244 when downloaded to image processing device 212 may be executed by image processor 214.

The processor 214 may be communicatively coupled to the memory device 216, and the processor 214 may be configured to execute computer executable instructions stored thereon. The processor 214 may send or receive medical images 246 to memory 216. For example, the processor 214 may receive medical images 246 from the image acquisition device 232 via the communication interface 218 and network 220 to be stored in memory 216. The processor 214 may also send medical images 246 stored in memory 216 via the communication interface 218 to the network 220 be either stored in database 224 or the hospital database 226.

Further, the processor 214 may utilize software programs 244 (e.g., a treatment planning software) along with the medical images 246 and patient data 245 to create the radiation therapy treatment plan 242. Medical images 246 may include information such as imaging data associated with a patient anatomical region, organ, or volume of interest segmentation data. Patient data 245 may include information such as (1) functional organ modeling data (e.g., serial versus parallel organs, appropriate dose response models, etc.); (2) radiation dosage data (e.g., dose-volume histogram (DVH) information; or (3) other clinical information about the patient and course of treatment (e.g., other surgeries, chemotherapy, previous radiotherapy, etc.).

In addition, the processor 214 may utilize software programs to generate intermediate data such as updated parameters to be used, for example, by a neural network model; or generate intermediate 2D or 3D images, which may then subsequently be stored in memory 216. The processor 214 may subsequently then transmit the executable radiation therapy treatment plan 242 via the communication interface 218 to the network 220 to the radiation therapy device 230, where the radiation therapy plan will be used to treat a patient with radiation. In addition, the processor 214 may execute software programs 244 to implement functions such as image conversion, image segmentation, deep learning, neural networks, and artificial intelligence. For instance, the processor 214 may execute software programs 244 that train or contour a medical image; such software 244 when executed may train a boundary detector, or utilize a shape dictionary.

The processor 214 may be a processing device, include one or more general-purpose processing devices such as a microprocessor, a central processing unit (CPU), a graphics processing unit (GPU), an accelerated processing unit (APU), or the like. More particularly, the processor 214 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 214 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 214 may be a special-purpose processor, rather than a general-purpose processor. The processor 214 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 214 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 214 may also include accelerated processing units such as the Xeon Phi™ family manufactured by Intel™. The disclosed embodiments are not limited to any type of processor(s) otherwise configured to meet the computing demands of identifying, analyzing, maintaining, generating, or providing large amounts of data or manipulating such data to perform the methods disclosed herein. In addition, the term "processor" may include more than one processor, for example, a multi-core design or a plurality of processors each having a multi-core design. The processor 214 may execute sequences of computer program instructions, stored in memory 216, to perform various operations, processes, methods that will be explained in greater detail below.

The memory device 216 may store medical images 246. In some embodiments, the medical images 246 may include one or more MRI image (e.g., 2D MRI 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer generated synthetic images (e.g., pseudo-CT images) and the like. Further, the medical images 246 may also include medical image data, for instance, training images, and ground truth images, contoured images, and dose images. In an embodiment, the medical images 246 may be received from the image acquisition device 232. Accordingly, image acquisition device 232 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 246 may be received and stored in any type of data or any type of format that the image processing device 212 may use to perform operations consistent with the disclosed embodiments. The memory device 216 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 214, or any other type of computer device. The computer program instructions may be accessed by the processor 214, read from the ROM, or any other suitable memory location, and loaded into the RAM for execution by the processor 214. For example, the memory 216 may store one or more software applications. Software applications stored in the memory 216 may include, for example, an operating system 243 for common computer systems as well as for software-controlled devices. Further, the memory 216 may store an entire software application, or only a part of a software application, that are executable by the processor 214. For example, the memory device 216 may store one or more radiation therapy treatment plans 242.

The image processing device 212 may communicate with the network 220 via the communication interface 218, which may be communicatively coupled to the processor 214 and the memory 216. The Communication interface 218 may provide communication connections between the image processing device 212 and radiotherapy system 200 components (e.g., permitting the exchange of data with external devices). For instance, the communication interface 218 may in some embodiments have appropriate interfacing circuitry to connect to the user interface 236, which may be a hardware keyboard, a keypad, or a touch screen through which a user may input information into radiotherapy system 200.

Communication interface 218 may include, for example, a network adaptor, a cable connector, a serial connector, a USB connector, a parallel connector, a high-speed data transmission adaptor (e.g., such as fiber, USB 3.0, Thunderbolt, and the like), a wireless network adaptor (e.g., such as a WiFi adaptor), a telecommunication adaptor (e.g., 3G, 4G/LTE and the like), and the like. Communication interface 218 may include one or more digital or analog communication devices that permit image processing device 212 to communicate with other machines and devices, such as remotely located components, via the network 220.

The network 220 may provide the functionality of a local area network (LAN), a wireless network, a cloud computing environment (e.g., software as a service, platform as a service, infrastructure as a service, etc.), a client-server, a wide area network (WAN), and the like. For example, network 220 may be a LAN or a WAN that may include other systems S1 (238), S2 (240), and S3 (241). Systems S1, S2, and S3 may be identical to image processing device 212 or may be different systems. In some embodiments, one or more of systems in network 220 may form a distributed computing/simulation environment that collaboratively performs the embodiments described herein. In some embodiments, one or more systems S1, S2, and S3 may include a CT scanner that obtains CT images (e.g., medical images 246). In addition, network 220 may be connected to internet 222 to communicate with servers and clients that reside remotely on the internet.

Therefore, network 220 may allow data transmission between the image processing device 212 and a number of various other systems and devices, such as the OIS 228, the radiation therapy device 230, and the image acquisition device 232. Further, data generated by the OIS 228 or the image acquisition device 232 may be stored in the memory 216, the database 224, or the hospital database 226. The data may be transmitted/received via network 220, through communication interface 218 in order to be accessed by the processor 214, as required.

The image processing device 212 may communicate with database 224 through network 220 to send/receive a plurality of various types of data stored on database 224. For example, database 224 may include machine data that is information associated with a radiation therapy device 230, image acquisition device 232, or other machines relevant to radiotherapy. Machine data information may include radiation beam size, arc placement, beam on and off time duration, machine parameters, segments, multi-leaf collimator (MLC) configuration, gantry speed, MrII pulse sequence, and the like. Database 224 may be a storage device and may be equipped with appropriate database administration software programs. One skilled in the art would appreciate that database 224 may include a plurality of devices located either in a central or a distributed manner.

In some embodiments, database 224 may include a processor-readable storage medium (not shown). While the processor-readable storage medium in an embodiment may be a single medium, the term "processor-readable storage medium" should be taken to include a single medium or multiple media (e.g., a centralized or distributed database, or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium may be or may include one or more volatile, non-transitory, or non-volatile tangible computer-readable media.

Image processor 214 may communicate with database 224 to read images into memory 216 or store images from memory 216 to database 224. For example, the database 224 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, etc.) that the database 224 received from image acquisition device 232. Database 224 may store data to be used by the image processor 214 when executing software program 244, or when creating radiation therapy treatment plans 242. Database 224 may store the data produced by the trained neural network including the network parameters constituting the model learned by the network and the resulting predicted data. The image processing device 112 may receive the imaging data 246 (e.g., 2D MRI slice images, CT images, 2D Fluoroscopy images, X-ray images, 3D MRI images, 4D MRI images, etc.) either from the database 224, the radiation therapy device 230 (e.g., a MRI-Linac, and or the image acquisition device 232 to generate a treatment plan 242.

In an embodiment, the radiotherapy system 200 may include an image acquisition device 232 that may acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 232 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 232 may be stored within database 224 as either imaging data or test data. By way of example, the images acquired by the imaging acquisition device 232 may be also stored by the image processing device 212, as medical image data 246 in memory 216.

In an embodiment, for example, the image acquisition device 232 may be integrated with the radiation therapy device 230 as a single apparatus (e.g., a MRI device combined with a linear accelerator, also referred to as an "MRI-Linac." Such an MRI-Linac may be used, for example, to determine a location of a target organ or a target tumor in the patient, so as to direct radiation therapy accurately according to the radiation therapy treatment plan 242 to a predetermined target.

The image acquisition device 232 may be configured to acquire one or more images of the patient's anatomy for a region of interest (e.g., a target organ, a target tumor or both). Each image, typically a 2D image or slice, may include one or more parameters (e.g., a 2D slice thickness, an orientation, and a location, etc.). In an embodiment, image acquisition device 232 may acquire a 2D slice in any orientation. For example, an orientation of the 2D slice may include a sagittal orientation, a coronal orientation, or an axial orientation. The processor 214 may adjust one or more parameters, such as the thickness or orientation of the 2D slice, to include the target organ or target tumor. In an embodiment, 2D slices may be determined from information such as a 3D MRI volume. Such 2D slices may be acquired by the image acquisition device 232 in "near real-time" while a patient is undergoing radiation therapy treatment, for example, when using the radiation therapy device 230. "Near real-time" meaning acquiring the data in milliseconds or less duration.

The image processing device 212 may generate and store radiation therapy treatment plans 242 for one or more patients. The radiation therapy treatment plans 242 may provide information about a particular radiation dose to be applied to each patient. The radiation therapy treatment plans 242 may also include other radiotherapy information, such as beam angles, dose-histogram-volume information, the number of radiation beams to be used during therapy, the dose per beam, and the like.

The image processor 214 may generate the radiation therapy treatment plan 242 by using software programs 244 such as treatment planning software, such as Monaco®, manufactured by Elekta AB of Stockholm, Sweden. In order to generate the radiation therapy treatment plans 242, the image processor 214 may communicate with the image acquisition device 232 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 200 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 232 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software, such as using one or more techniques as shown and described elsewhere herein.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 142 that may be stored in memory 216 or database 224. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 212 may generate a tailored radiation therapy treatment plan 242 having these parameters in order for the radiation therapy device 230 to provide radiotherapy treatment to the patient.

In addition, the radiotherapy system 200 may include a display device 234 and a user interface 236. The display device 234 may include one or more display screens that display medical images, interface information, treatment planning parameters (e.g., contours, dosages, beam angles, etc.) treatment plans, a target, localizing a target or tracking a target, or any related information to the user. The user interface 236 may be a keyboard, a keypad, a touch screen or any type of device that a user may input information to radiotherapy system 200. Alternatively, the display device 234 and the user interface 236 may be integrated into a device such as a tablet computer (e.g., Apple iPad®, Lenovo Thinkpad®, Samsung Galaxy®, etc.).

Furthermore, a subset or an entirety of the components of the radiotherapy system 200 may be implemented as a virtual machine (e.g., VMWare™, Hyper-V™, and the like). For instance, a virtual machine may be software that functions as hardware. Therefore, a virtual machine may include at least one or more virtual processors, one or more virtual memories, and one or more virtual communication interfaces that together function as hardware. For example, the image processing device 212, the OIS 228, the image acquisition device 232 could be implemented as a virtual machine. Given the processing power, memory, and computational capability available, the entire radiotherapy system 200 could be implemented as a virtual machine.

Figure 3:
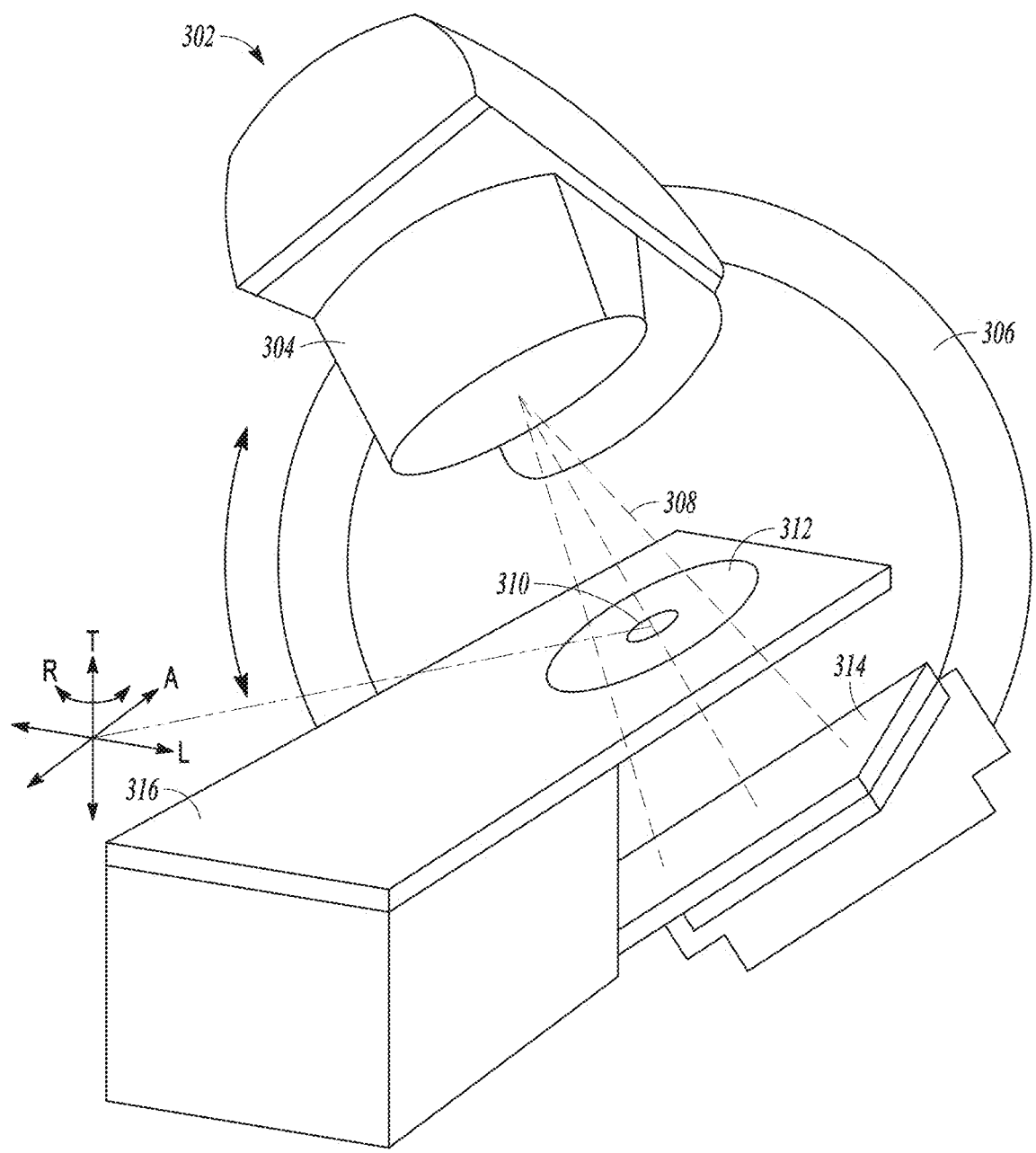
FIG. 3 illustrates an example including a radiation therapy device that may include a radiation source, such as an X-ray source or a linear accelerator, a couch, an imaging detector, and a radiation therapy output.

FIG. 3 illustrates an example including a radiation therapy device 302 that may include a radiation source, such as an X-ray source or a linear accelerator, a couch 316, an imaging detector 314, and a radiation therapy output 304. The radiation therapy device 302 may be configured to emit a radiation beam 308 to provide therapy to a patient. The radiation therapy output 304 may include one or more attenuators or collimators, such as a multi-leaf collimator (MLC). A patient may be positioned in a region 312, supported by the treatment couch 316 to receive a radiation therapy dose according to a radiation therapy treatment plan.

The radiation therapy output 304 may be mounted or attached to a gantry 306 or other mechanical support. One or more chassis motors (not shown) may rotate the gantry 306 and the radiation therapy output 304 around couch 316 when the couch 316 is inserted into the treatment area. In an embodiment, gantry 306 may be continuously rotatable around couch 316 when the couch 316 is inserted into the treatment area. In another embodiment, gantry 306 may rotate to a predetermined position when the couch 316 is inserted into the treatment area. For example, the gantry 306 may be configured to rotate the therapy output 304 around an axis ("A"). Both the couch 316 and the radiation therapy output 304 may be independently moveable to other positions around the patient, such as moveable in transverse direction ("T"), moveable in a lateral direction ("L"), or as rotation about one or more other axes, such as rotation about a transverse axis (indicated as "R") A controller communicatively connected to one or more actuators (not shown) may control the couch 316 movements or rotations in order to properly position the patient in or out of the radiation beam 308 according to a radiation therapy treatment plan. As both the couch 316 and the gantry 306 are independently moveable from one another in multiple degrees of freedom, which allows the patient to be positioned such that the radiation beam 308 precisely may target the tumor.

The coordinate system (including axes A, T, and L) shown in FIG. 3 may have an origin located at an isocenter 310. The isocenter may be defined as a location where the central axis of the radiation therapy beam 308 intersects the origin of a coordinate axis, such as to deliver a prescribed radiation dose to a location on or within a patient. Alternatively, the isocenter 310 may be defined as a location where the central axis of the radiation therapy beam 308 intersects the patient for various rotational positions of the radiation therapy output 304 as positioned by the gantry 306 around the axis A.

Gantry 306 may also have an attached imaging detector 314. The imaging detector 214 preferably located opposite to the radiation source 204, and in an embodiment, the imaging detector 214 may be located within a field of the therapy beam 208. The imaging detector 314 may be mounted on the gantry 306 preferably opposite the radiation therapy output 304, such as to maintain alignment with the therapy beam 308. The imaging detector 314 rotating about the rotational axis as the gantry 306 rotates. In an embodiment, the imaging detector 314 may be a flat panel detector (e.g., a direct detector or a scintillator detector). In this manner, the imaging detector 314 may be used to monitor the therapy beam 308 or the imaging detector 314 may be used for imaging the patient's anatomy, such as portal imaging. The control circuitry of radiotherapy device 302 may be integrated within system 100 or remote from it.

In an illustrative embodiment, one or more of the couch 316, the therapy output 304, or the gantry 306 may be automatically positioned, and the therapy output 304 may establish the therapy beam 308 according to a specified dose for a particular therapy delivery instance. A sequence of therapy deliveries may be specified according to a radiation therapy treatment plan, such as using one or more different orientations or locations of the gantry 306, couch 316, or therapy output 304. The therapy deliveries may occur sequentially, but may intersect in a desired therapy locus on or within the patient, such as at the isocenter 310. A prescribed cumulative dose of radiation therapy may thereby be delivered to the therapy locus while damage to tissue nearby the therapy locus may be reduced or avoided.

The example of FIG. 3 generally illustrates an embodiment of a radiation therapy device configured to provide radiotherapy treatment to a patient, including a configuration where a radiation therapy output may be rotated around a central axis (e.g., an axis "A"). Other radiation therapy output configurations may be used. For example, a radiation therapy output may be mounted to a robotic arm or manipulator having multiple degrees of freedom. In yet another embodiment, the therapy output may be fixed, such as located in a region laterally separated from the patient, and a platform supporting the patient may be used to align a radiation therapy isocenter with a specified target locus within the patient. In another embodiment, a radiation therapy device may be a combination of a linear accelerator and an image acquisition device. In some embodiments, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Figure 4:
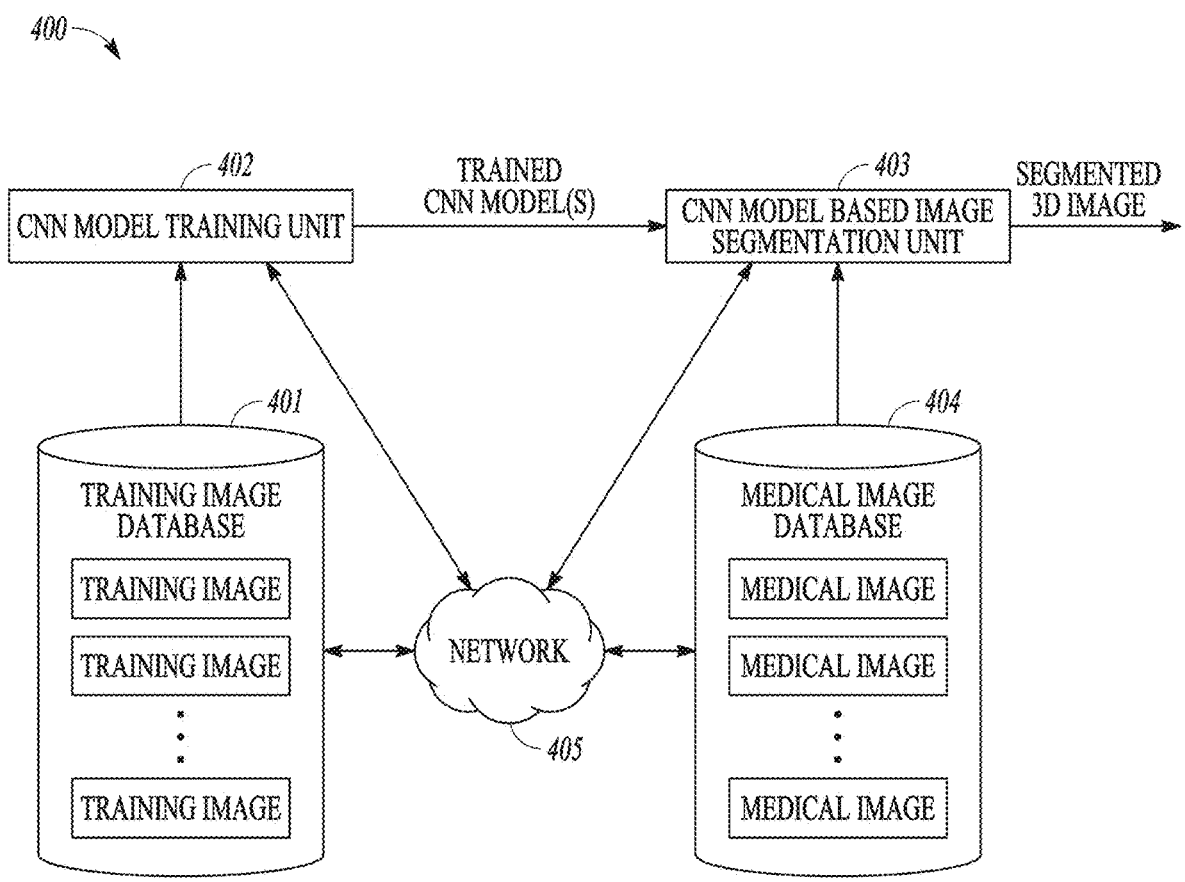
FIG. 4 illustrates an example including an image segmentation system for segmenting 3D images, such as using first and second CNN models, as mentioned in relation to other examples.

FIG. 4 illustrates an example including an image segmentation system 400 for segmenting 3D images, such as using first and second CNN models, as mentioned in relation to other examples described in this document. The segmentation system 400 may be included as a portion of the radiotherapy system 200 as shown in FIG. 2, or the segmentation system 400 of FIG. 4 may be communicatively coupled to such a radiotherapy system. As shown in FIG. 4, the image segmentation system 400 may include components for performing two stages, a training stage and a segmentation stage. To perform the training stage, the image segmentation system 400 may include a training image database 401 and a CNN model training unit 402. To perform the segmentation stage, the image segmentation system 400 may include a CNN model-based image segmentation unit 403 and a medical image database 404. In some embodiments, the image segmentation system 400 may include more or less of the components shown in FIG. 4. For example, when a CNN model for image segmentation is pre-trained and provided, the image segmentation system 400 may only include the segmentation unit 403 and the medical image database 404. The Image segmentation system 400 may optionally include a network 405. In some embodiments, the network 405 may be replaced by wired data communication systems or devices.

In some embodiments, the various components of the image segmentation system 400 may be located remotely from each other or in different spaces, and be connected through the network 405 as shown in FIG. 4. In some embodiments, certain components of the image segmentation system 400 may be located on the same site or inside one device. For example, the training image database 401 may be located on site with the CNN model training unit 402, or be part of the CNN model training unit 402. As another example, the CNN model training unit 402 and the segmentation unit 403 may be inside the same computer or processing device.

As shown in FIG. 4, the CNN model training unit 402 may communicate with the training image database 401 to receive one or more sets of training images. The sets of training images stored in the training image database 401 may be obtained from a medical image database, for example, a medical image database containing previously acquired medical images during radiotherapy treatment sessions. Each set of training images may include a 3D image and its corresponding 3D ground truth label map that associates an anatomical structure to each of the voxels of the 3D image. The 3D image may be selectively divided to one or more sequential stacks of adjacent 2D images. The 3D ground truth label map may be divided to sequential 2D ground truth label maps, respectively corresponding to the sequential stacks of adjacent 2D images, and pixels of the 2D ground truth label maps are associated with known anatomical structures. The number of adjacent 2D images in each stack may be determined based on various factors, such as the size of the 3D image, a specific framework of the CNN model, the relationship between the anatomical structures in the adjacent 2D images along an axis orthogonal to the 2D image, or the application of the segmentation.

In some embodiments, a stack of adjacent 2D images includes an odd number of images, such as 3, 5, 7, or any suitable odd number. In such instances, the ground truth label map provides a known anatomical structure label for each pixel of the middle image of the stack. In other embodiments, a stack of adjacent 2D images includes an even number of images, such as 2, 4, 6, or any suitable even number. In such instances, the ground truth label map provides a known anatomical structure label for each pixel of one of the two middle images of the stack. Consistent with the disclosed embodiments, the training images may be acquired using various imaging modalities, including MRI, functional MRI (e.g., fMRI, DCE-MRI and diffusion MRI), CT, CBCT, Spiral CT, PET, SPECT, X-ray, optical tomography, fluorescence imaging, ultrasound imaging, and radiotherapy portal imaging, etc. In some embodiments, the training data may be collected from an Oncology Information System or other centralized repository. For example, the training images may be acquired by the image acquisition device 440.

CNN model training unit 402 may use the training images received from training image database 401 to train a CNN model for performing image segmentation of new 3D images. CNN model training unit 402 may include a processor and a non-transitory computer-readable medium. The processor may conduct the training by performing instructions of a training process stored in the computer-readable medium. The CNN model training unit 402 may additionally include input and output interfaces to communicate with the training image database 401, network 405, or a user interface (not shown). The user interface may be used for selecting sets of training images, adjusting one or more parameters of the training process (e.g., the number of adjacent image slices in each stack), selecting or modifying a framework of a CNN model, or manually or semi-automatically segmenting an image for training. The CNN model training unit 402 may be implemented with hardware specially programmed by software that performs the training process.

The segmentation unit 403 may receive at least one trained CNN model from the CNN model training unit 402. The segmentation unit 403 may include a processor and a non-transitory computer-readable medium (as mentioned in relation to the system 200 of FIG. 2). The processor may conduct the segmentation of a 3D image by performing instructions of an image segmentation process stored in the medium. The segmentation unit 403 may additionally include input and output interfaces to communicate with the medical image database 404, the network 405, or a user interface. The user interface may be used for selecting a 3D image to be segmented, initiating the segmentation process, displaying the segmented 3D image or a 3D label map, or performing further analysis based on the segmented image or the 3D label map. Various techniques for performing CNN-based segmentation are described in relation to the examples elsewhere herein, such as shown and described in relation to FIG. 5, FIG. 6A, FIG. 6B, FIG. 7, FIG. 8, FIG. 9, or FIG. 10.

The segmentation unit 403 may communicate with medical image database 404 to receive one or more 3D images. The 3D images stored in medical image database 404 may be obtained from a medical image database, which contains 2D or 3D images of radiotherapy treatment sessions, for example. As described herein, the 3D images may be reconstructed from 2D projection images acquired by medical imaging devices, such as image acquisition device 440. These 3D images are typically not segmented yet. The segmentation unit 403 may use at least one trained CNN model received from CNN model training unit 402 to predict the anatomical structure each voxel of a 4D image represents. When the image segmentation is completed, segmentation unit 403 may output a 3D label map, associating each voxel of the 3D image to an anatomical structure. The 3D label map may be displayed in the user interface, or stored in medical image database 404 for further use in treatment planning. In some embodiments, the segmented image may be automatically stored in training image database 401 and become a training image.

The 3D images to be segmented may be acquired using various imaging modalities, including MRI, functional MRI (e.g., fMRI, DCE-MRI and diffusion MRI), CT, CBCT, Spiral CT, PET, SPECT, X-ray, optical tomography, fluorescence imaging, ultrasound imaging, and radiotherapy portal imaging, etc. In some embodiments, the medical image database 404 may be an integrated part of the segmentation unit 403, or located on the same site of the segmentation unit 403, such as in a radiotherapy treatment room. The network 105 may provide connections between any of the above described components in the image segmentation system 400. For example, the network 405 may be a local area network (LAN), a wireless network, a cloud computing environment (e.g., software as a service, platform as a service, infrastructure as a service), a client-server, a wide area network (WAN), etc.

Figure 5:
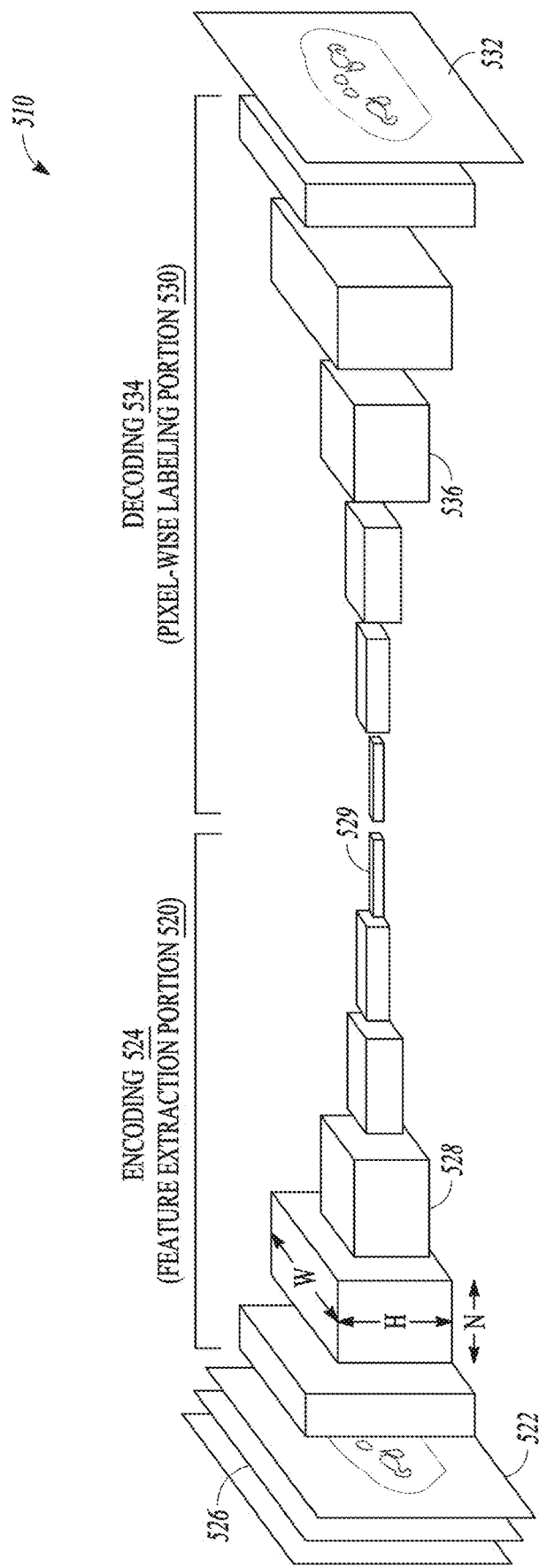
FIG. 5 illustrates an example including at least a portion of a CNN model for image segmentation.

FIG. 5 illustrates an example generally showing a structure for a CNN (e.g., a DCNN) model that may be used for image segmentation. As shown in FIG. 5, a CNN model for image segmentation may receive a stack of adjacent 2D images as input and outputs a predicted 2D label map of one of the images in the middle of the stack. As described above, if the stack of adjacent 2D images includes an odd number of images, the 2D label map provides structure labels of the middle image of the stack. Alternatively, if the stack of adjacent 2D images includes an even number of images, the 2D label map provides structure labels of one of the two middle images of the stack.

As shown in FIG. 5, the CNN model 510 may generally include two portions: a first feature extraction portion 520 and a second pixel-wise labeling portion 530. Feature extraction portion 520 may extract one or more features of an input stack of adjacent 2D images 522. The feature extraction portion 520 forms the encoding portion of the CNN model 524 to receive input stack of adjacent 2D images 522 and to output at least one feature vector or matrix representing the features of the input stack. The pixel-wise labeling portion 530 or decoding portion 534 of the CNN model builds on the output of the feature extraction portion 520 to gradually generate a 2D label map 532 corresponding to a middle image 526 of input stack of adjacent 2D images 522.

Use of a stack of adjacent 2D images that contain dependent structure information both for training and as the input of the CNN model 510 improves the accuracy of the prediction of output 2D label map 532 by CNN model 510. This further improves the accuracy of the predicted 3D label map of a 3D image constructed from 2D label maps predicted for each image slice of the 3D image. The dependent structure information may refer to a spatially dependent relationship between the anatomical structures shown in the stack of adjacent 2D images along the axis orthogonal to the anatomical plane of the 2D images. The shape and type of an anatomical structure represented by a first set of pixels in a first image of the stack may also be represented by a second set of pixels in a second image adjacent to the first image. This is because the spatial neighboring of the first and second images along the axis orthogonal to the anatomical plane allows for some dependency or continuity of the anatomical structures shown in these images. Therefore, the shape, size, or type of an anatomical structure in one image may provide information of the shape, size, or type of the anatomical structure in another adjacent image along the same plane.

When the stack of adjacent 2D images includes three sequential images, e.g., first, second, and third image slices stacked in sequence, an anatomical structure may be shown in both a first set of pixels in the first image slice of the stack and a third set of pixels in a third image slice of the stack, but not in a corresponding second set of pixels (e.g., pixels having similar spatial locations as those of the first or third set of pixels) of the second image slice that is between and adjacent to the first and third image slices. In such instances, the corresponding pixels in the second image slice may be incorrectly labeled. Such discontinuity of the anatomical structure in the stack of three adjacent 2D image slices may be used as dependent structure information for training CNN model 510.

In a stack of three adjacent 2D images, e.g., first, second, and third image slices stacked in sequence, both a first set of pixels in the first image slice of the stack and a third set of pixels in the third image slice may indicate the background, but a corresponding second set of pixels of the second image slice between and adjacent to the first and third image slices may indicate an anatomical structure. The corresponding pixels in the second image slice may be subject to noise that generates a false positive signal. Such discontinuity of the background in the stack of three adjacent 2D image slices may also be used as dependent structure information for training CNN model 510.

Different types of dependent structure information may be selectively used based on various factors, such as the number of adjacent images in the stack, the types, shapes, sizes, positions, and/or numbers of the anatomical structures to be segmented, or the imaging modality used for obtaining the images. As described above, the use of such dependent structure information of stacks of adjacent 2D images obtained from a 3D image improves the accuracy for segmenting the 3D image or generating a 3D label map.

Various components and features of CNN model 510 used in the embodiments of the present disclosure are described in detail below. In some embodiments, the encoding portion 524 of the CNN model 510 includes an input layer, e.g., a stack of adjacent 2D images 522. Because a stack of adjacent 2D images are used as the input, the input layer has a volume, whose spatial dimensions are determined by the width and height of the 2D images, and the number of images in the stack can be considered as the number of channels of the input layer. As described herein, the channels of the input layer of CNN model 510 may be adjusted to match the number of images in input stack of adjacent 2D images 522.

The encoding portion 524 of the CNN model 510 may include one or more convolutional layers 528. Each convolutional layer 528 may have a plurality of parameters, such as the width ("W") and height ("H") determined by the upper input layer (e.g., the size of the input of convolutional layer 528), and a count of filters or kernels ("N") in the layer and their sizes. The number of filters may be referred to as the channels of the convolutional layer. Therefore, each convolutional layer 528 may be described in terms of a 3D volume as shown in FIG. 5. The input of each convolutional layer 528 is convolved with one filter across its width and height and produces a 2D activation map or feature map corresponding to that filter. The convolution is performed for all filters of each convolutional layer, and the resulting activation maps or feature maps are stacked along the channel dimension, generating a 3D output. The output of a preceding convolutional layer may be used as input to the next convolutional layer.

Figure 6A:
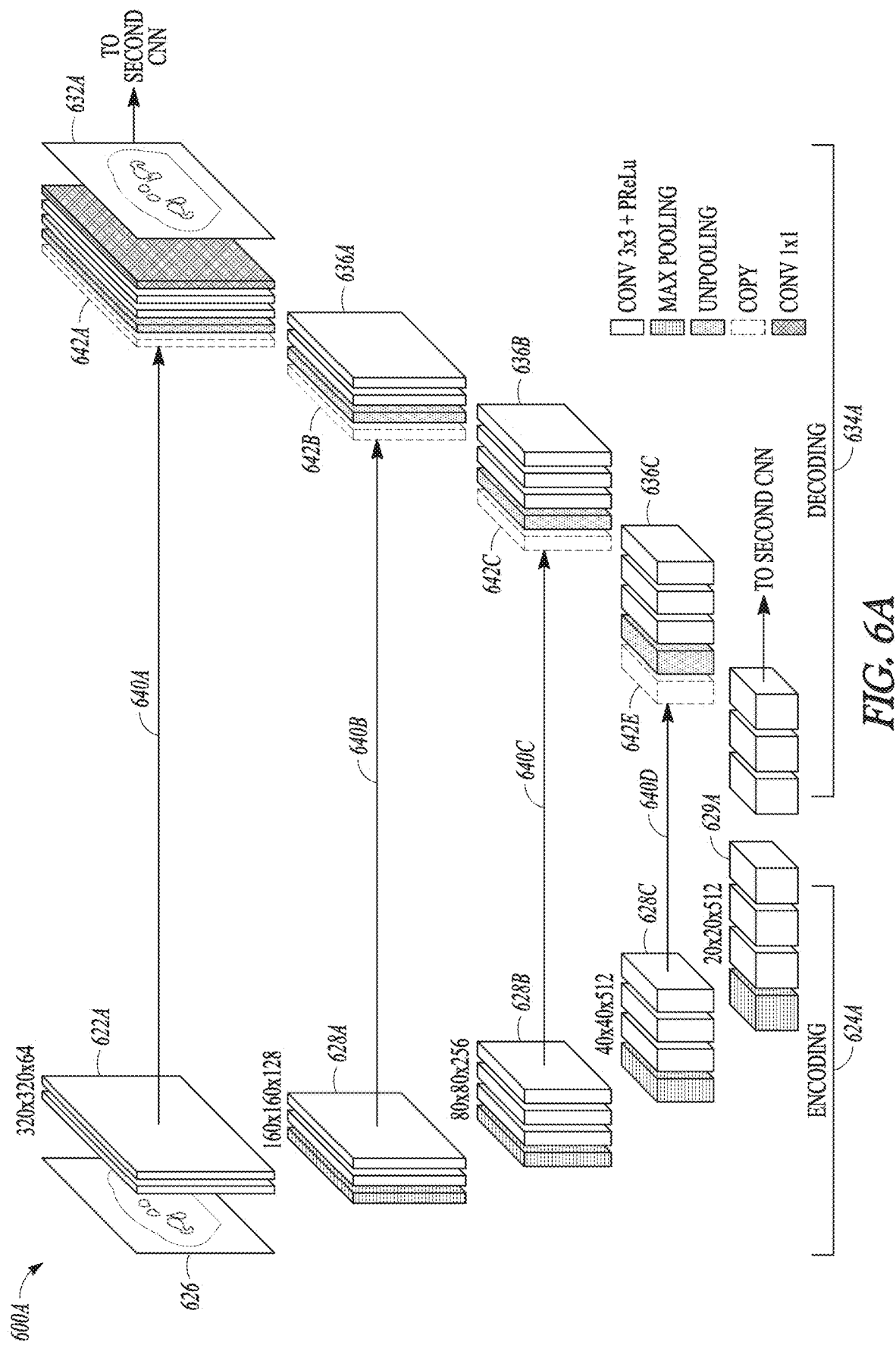
FIG. 6A and FIG. 6B illustrate generally examples that include a deep convolutional neural network (DCNN) architecture.
Figure 6B:
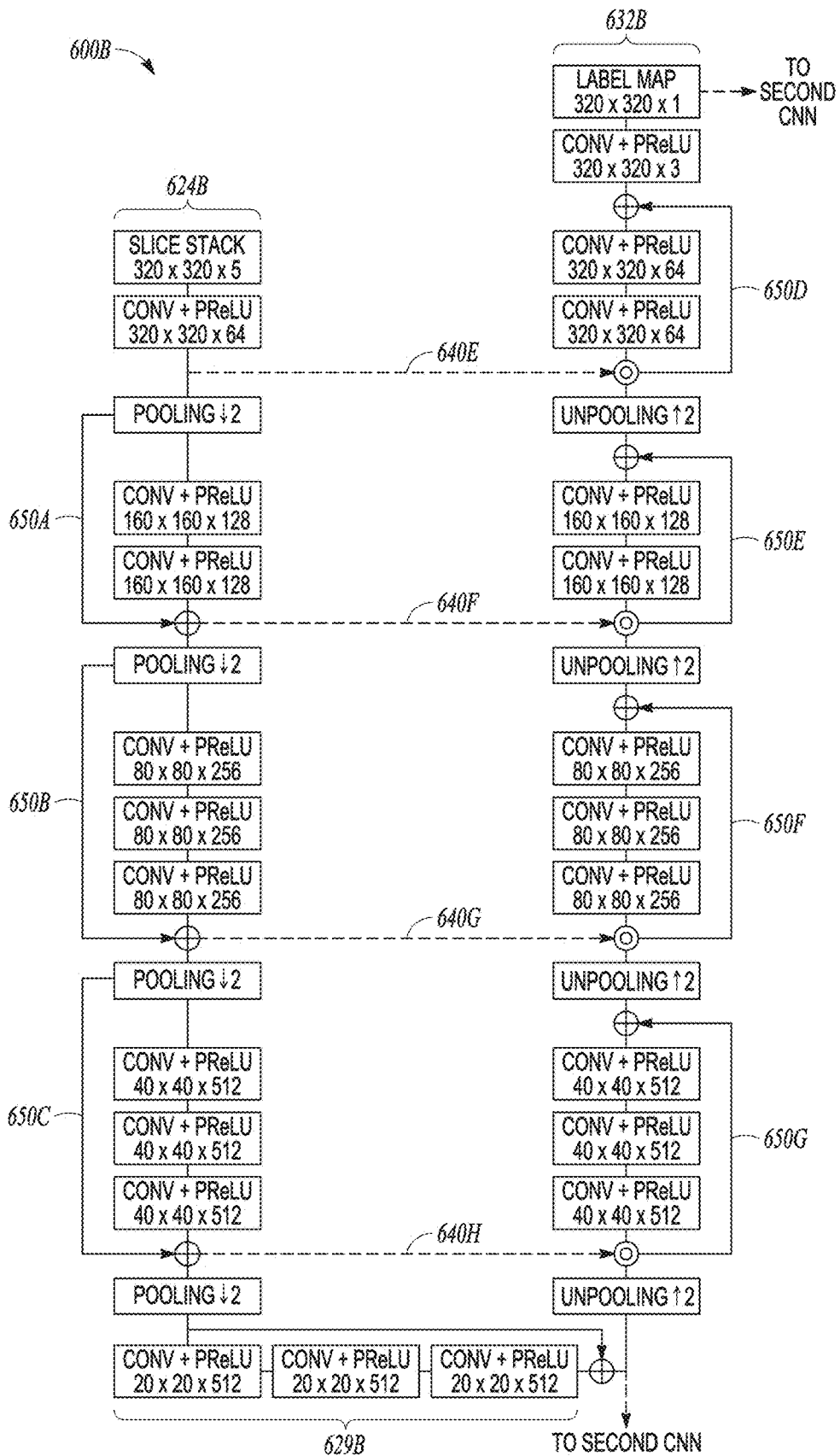

In some embodiments, the encoding portion 524 of the CNN model 510 includes one or more pooling layers (shown illustratively in the examples of FIG. 6A and FIG. 6B). A pooling layer may be added between two successive convolutional layers 528 in CNN model 510. A pooling layer may operate independently on every channel of its input (e.g., an activation map or feature map from a previous convolutional layer), and reduces the spatial dimension by performing a form of non-linear down-sampling. In certain examples, information from a non-adjacent layer may "skip" intervening layers and may be aggregated together with the output of a later convolutional layer before passing through a pooling layer, as shown illustratively in FIG. 6A and FIG. 6B. As shown in FIG. 5, a function of the pooling layers may include progressively reducing a spatial dimension of the extracted activation maps or feature maps to reduce a count of parameters and computation in the network, and to control over-fitting. A count and placement of the pooling layers may be determined based on various factors, such as the design of the convolutional network architecture, the size of the input, the size of convolutional layers 528, or application of CNN model 510.

Various non-linear functions may be used to implement the pooling layers. For example, max pooling may be used. Max pooling may partition an image slice of the input into a set of overlapping or non-overlapping sub-regions with a predetermined stride. For each sub-region, max pooling outputs a maximum value amongst corresponding sub-regions within the partition. This effectively downsamples every slice of the input along both its width and its height while the channel dimension remains unchanged. Other suitable functions may be used for implementing the pooling layers, such as average pooling or even L2-norm pooling.

The CNN model 510 may selectively include one or more additional layers in its encoding portion 524. As a non-limiting example, a Rectfied Linear Unit (ReLu) layer or Parametric ReLU (PReLU) may be selectively added after a convolutional layer to generate an intermediate activation map or feature map. For example, a ReLu layer may desirably increase the nonlinear properties of the predictor function and the overall of CNN model 510 without affecting the respective dimensions of convolutional layers 528. Additionally, the ReLu layer may reduce or avoid saturation during a backpropagation training process.

One or more fully connected layers 529 may be added after the convolutional layers or the pooling layers. The fully connected layers have a full connection with all activation maps or feature maps of the previous layer. For example, a fully connected layer may take the output of the last convolutional layer or the last pooling layer as the input in vector form, and perform high-level determination and output a feature vector arranged along the channel dimension. The vector may contain information of the anatomical structures in the input stack of images 522 of CNN model 510. According to various examples herein, such as mentioned in relation to FIG. 6A and FIG. 6B, information from the output layer extracted from 2D imaging slices according to a 2D or "2.5D" CNN model may be used to identify a sub-region of 3D imaging data. Such output data from the CNN model 510 may also be used in concert with a 3D CNN applied to an identified sub-region.

In the second portion of CNN model 510, pixel-wise labeling may be performed using the one or more features extracted by convolutional neural network 524 as the input to generate a predicted 2D label map 532. The 2D label map may provide structure labels of the middle images of the stack of adjacent 2D images. In an example, the 2D label map may be used to automatically determine a sub-region of 3D imaging to which a second, 3D CNN model may be applied.

A patch-based approach may be used for predicting 2D label map 532 of middle image 526 of input stack of adjacent 2D images 522. Each image in the stack of adjacent 2D images may be similarly divided into overlapping or non-overlapping rectangular patches, each having a central pixel. This generates a stack of adjacent 2D image patches. A stack of 2D image patches may be used as both training data and input of CNN model 510. The patches may be designed such that the central pixels of the patches together substantially constitute a whole 2D image. The CNN model 510 may classify the central pixel of a middle patch of each stack of patches (e.g., predicting the anatomical structure represented by the central pixel). For example, the CNN model 510 may predict a feature vector of the central pixel of the middle patch in the stack, thereby allowing for classifying the anatomical structure of the central pixel. Such classification is performed repeatedly until all central pixels of the middle patches of all stacks of adjacent 2D image patches are classified or labeled, thereby achieving segmentation of the middle image of the stack of adjacent 2D images. In the above-described patch-based approach, pixel-wise labeling of middle image 526 of input stack of adjacent 2D images 522 may be performed when all the central pixels constituting the whole middle image 526 are classified.

In another example, a fully-convolutional approach may be used for predicting 2D label map 532 corresponding to a middle image 526 of input stack of adjacent 2D images 522, such as using a "fully convolutional network" (FCN). In such instances, the 2D label map 532 of middle image 526 may be generated as the output of CNN model 510 based on input stack of adjacent 2D images 522. The encoding portion 524 in CNN model 510 is used for extracting an activation map or a feature map as an output, which is received by a decoding portion 534 that includes one or more operation layers to predict the 2D label map. In such instances, the final layer of the encoding portion 524 may be a convolutional layer that outputs the activation map or feature map.

A decoding portion 534 may be used as a portion of the CNN model 510 to perform the pixel-wise labeling. The decoding portion 534 may be a mirrored version of encoding portion 524 of the CNN model 510. Various functions may be used, such as backwards upsampling or unpooling (e.g., bilinear or nonlinear interpolation), and backwards convolution (which may be referred to colloquially as "deconvolution"). Contrary to the encoding portion 524 structure that progressively reduces the spatial dimensions of the extracted activation maps or feature maps, the decoding portion 534 enlarges the intermediate activation maps or feature maps by using a selection of deconvolution layers 536 or unpooling layers. An unpooling layer (e.g., an upsampling layer) may be used to place the pixels in the feature maps back to their previous or original pool location, thereby generating an enlarged, yet sparse activation map or feature map. A deconvolution layer may be used to associate a single pixel of an input activation map or feature map to multiple output pixels, thereby enlarging and increasing the density of the activation map or feature map.

The decoding portion 534 may be trained and used together with encoding portion 524 to predict a 2D label map. A loss layer may be included in CNN model 510 during model training. During the training of CNN model 510, the loss layer may determine how the network training penalizes the deviation between the predicted 2D label map and the 2D ground truth label map. The loss layer may be implemented by various suitable loss functions. For example, a cross-entropy loss function may be used as the final loss layer of the CNN model 510. In another approach, a Dice loss or adversarial loss technique can be used. When an adversarial loss is used, a loss layer can include another CNN model that is trained together with the CNN model 510 to automatically decide whether the predicted 2D label map closely resembles the ground truth or not.

Consistent with embodiments of the present disclosure, the image segmentation methods, systems, devices, or processes based on the above-described CNN models include two stages: a training stage that "trains" or "learns" the CNN model using training datasets that include 3D images labeled with different anatomical structures for each voxel, and a segmentation stage that uses the trained CNN model to predict the anatomical structure of each voxel of an input 3D image or label each voxel of an input 3D medical image to an anatomical structure. Various further examples are discussed below. The general structure of the convolutional neural network shown in FIG. 5 is also applicable to a 3D model, wherein a 3D image or a group of 3D images are provided as the model input rather than a stack of 2D images. In addition, for a 3D DCNN model, the kernel spatial dimension of the convolutional, de-convolutional, pooling, and unpooling layers will be 3D (width, height, depth) instead of 2D (width and height), and the activation or feature maps have a dimension of 4 (width, height, depth, channel) instead of 3 (width, height, channel).

FIG. 6A and FIG. 6B illustrate generally examples that may include a deep convolutional neural network (DCNN) architecture 600A and a DCNN architecture 600B, respectively. The DCNN 600A of FIG. 6A and the DCNN 600B FIG. 6B may be classified as "fully convolutional neural networks" (FCNs). FCNs generally allow the complete segmentation of an entire (e.g., 2D) image in a single pass instead of classifying the center pixel of a small image patch each time. In addition to being more efficient, using an entire image as input may offer much richer contextual information than a small image patch, which may lead to more reliable and more accurate segmentation results. Different FCN architectures may be used, such as having an encoding portion 624A (as in FIG. 6A) or encoding portion 624B (as in FIG. 6B). The encoding portion resembles a typical CNN that extracts a hierarchy of image features from low to high complexity. A decoding portion 634A (as in FIG. 6A) or decoding portion 634B (as in FIG. 6B) then transforms the features and gradually reconstructs the segmentation label map from coarser to finer resolution.

The architectures of the DCNN 600A and DCNN 600B are similar to the example of FIG. 5, but FIG. 6A and FIG. 6B show long-range connections 640A, 640B, and 640C (in FIG. 6A) and long-range connections 640E, 640F, and 640G (in FIG. 6B). FIG. 6B also illustrates short-range connections 650A, 650B, and 650C within the encoding portion 624B, along with short-range connections 650D, 650E, 650F, and 650G within the decoding portion 634B. Use of long range connections across the encoding and decoding portions (e.g., between portions 624A and 634A in FIG. 6A or between portions 624B and 634B in FIG. 6B) permits higher resolution features from the encoding portion (624A or 624B) to be used as inputs for (de)convolutional layers in the decoding portions (634A or 634B). Such a configuration enhances a capability of the decoding portion (634A or 634B) to generate high resolution predictions. These sorts of short-cuts also make the model 600A and the model 600B more flexible. For example, the model 600A and the model 600B may automatically through training learn to skip coarse level features (at the "bottom" of the network such as at layer 629A in FIG. 6A) if high resolution features (at the "top" of the network) are sufficient to produce accurate segmentation results. The long-range connections 640A, 640B, 640C, and 640D shown in FIG. 6A may be provided by taking an output of a corresponding convolutional layer to provide a corresponding copy 642A, 642B, 642C, and 642E, respectively.

Referring to the DCNN 600A of FIG. 6A, a 2.5D input stack may be provided to a first convolutional layer, such as having a spatial size of 320×320 and the convolutional layer has 64 filters or "channels." The input stack may be extracted as a group of adjacent 2D slices obtained from 3D imaging information, as an example. The input stack may include five (or any number of) 2D images including a center image 626. The DCNN 600A of FIG. 6A may include five different resolution layers, such as a first downsampled layer 628A having an output size of 160×160×128 channels, a second downsampled layer 628B having an output size of 80×80×256 channels, a third downsampled layer 628C having an output size of 40×40×512 layers, and a bottom layer 629A having an output size of 20×20×512 channels. An output of the bottom layer 629A may include feature-domain information (e.g., a feature map or feature vector set).

Downsampling may be achieved through pooling as described generally in other examples, such as above in relation to FIG. 5. The decoding portion 634A of the DCNN 600A of FIG. 6A may include upsampling or "deconvolutional" layers, such as a first upsampling layer 636C, a second upsampling layer 636B, and a third upsampling layer 636A. A final or output layer 632A may provide a label map at a resolution similar to or matching a resolution of the input 2D imaging data. According to various examples, either feature information at the layer 629A or label information from the output layer 632A may be used to identify a sub-region within 3D imaging information provided as an input to a second DCNN 600A, and such information may be used to perform full 3D analysis of the sub-region using a second DCNN.

Referring to the DCNN 600B of FIG. 6B, short-range residue connections 650A, 650B, 650C, 650D, 65GE, 650F, and 650G are shown, within the encoding portion 624B and decoding portion 634B, respectively. The residue connections help promote information propagation through the DCNN 600B both forward and backward and may improve model convergence or accuracy, particularly when the DCNN 600B is trained from scratch. In a manner similar to the examples of FIG. 5 and FIG. 6A, an input slice stack may be provided to an encoding portion 624B of the DCNN 600B. Various convolution and pooling operations may be performed, such as to providing downsampling (in the encoding portion 624B) or upsampling (in the decoding portion 634B). Pooling operations are shown and short-range or long-range connections, as mentioned above, may bypass certain convolutional layers. A bottom layer 629B may be used for other operations, such as providing feature-domain information. If a label map is desired, the decoding portion 634B of the DCNN 600B may be used to provide a 2D label map 632B as an output. According to various examples described herein, the label map may be used alone or aggregated, such as to determine a 3D sub-region for applying another (e.g., different) DCNN model. For example, the DCNN model 600A of FIG. 6A or the DCNN model 600B of FIG. 6B may be used as a 2D or "2.5D" model to assist in identifying a sub-region on which a 3D DCNN model is used for segmentation. The drawings of FIG. 6A and FIG. 6B illustrate a 2D or 2.5D model. A 3D DCNN model shares similar architecture, except that the input and output are 3D images, and the feature maps of every intermediate layers (convolutional, pooling, unpooling, deconvolutional) are 4D images instead of 3D.

Figure 7:
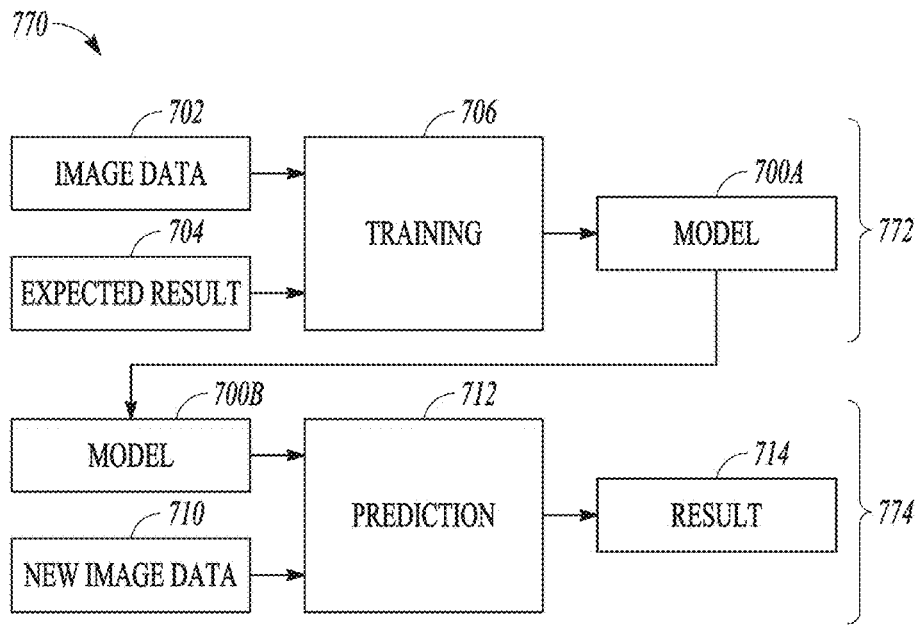
FIG. 7 illustrates generally an illustrative example of a deep convolutional neural network (DCNN) workflow including training and prediction arms.

FIG. 7 illustrates generally an illustrative example of a deep convolutional neural network (DCNN) workflow including a training arm 772 and a prediction arm 774. Generally, a DCNN model 700A represents an end-to-end mapping from the input imaging information (e.g., 2D slices) to a segmentation label map (e.g., a 2D label map). The model 700A parameters may be established from training data, such as by minimizing a loss function. One example of such a loss function includes a cross-entropy loss function, which may be represented as follows by EQN. 1:

$$L = -\frac{1}{N}\sum_{i=1}^{N}\sum_{c=0}^{5} w_i^c y_i^c \log P_i^c \quad [\text{EQN. 1}]$$

In EQN, 1, $P_i^c$ may represent a predicted probability of voxel i belonging to class c (background, left lung, right lung, heart, esophagus, and spinal cord in this example) and $y_i^2$ may represent a value corresponding to the ground truth. The variable $w_i^c$ may be used to represent a class dependent weighting factor. Empirically, in an illustrative example, the weights may be assigned as 0.2 for background, 1.0 for the lungs and the heart, and 2.0 for the remaining two structures in the five-OAR model. In the workflow shown in FIG. 7, training image data 702 may be provided along with "ground truth" expected results 704 to a training unit (as mentioned in relation to other examples herein). A loss function may be used to establish model 700A parameters as mentioned above in the training arm 772, or other techniques may be used to establish the model 700A parameters. The model may be provided for use in a prediction arm 774. New image data 710 may be provided as an input to be used in prediction 712 along with the model 700B parameters (as obtained from the model 700A trained in the arm 772), and a result 714 (such as a 2D label map or 3D segmentation information) may be provided. If two CNNs are used, such as a 2D or "2.5D" CNN as a first CNN and a 3D CNN as a second CNN, the workflow 770 shown in FIG. 7 may be performed separately to establish model 700 parameters for each CNN. The image data 702 may be site-specific, or may be Obtained from a centralized repository, such as representative of multiple clinical sites. Such training information may include one or more variations such as relating to resolution, contrast, region imaged, imaging equipment type or manufacturer, or other variations, such as to help provide model 700 parameters that are robust to such variations across one or more of patients, sites, or specific imaging equipment configuration. Generally, the phrase "segmented image" refers to 2D or 3D imaging information including a map of labeled anatomical (or other) features, such as pertinent to radiation therapy treatment planning or therapy delivery.

Figure 8:
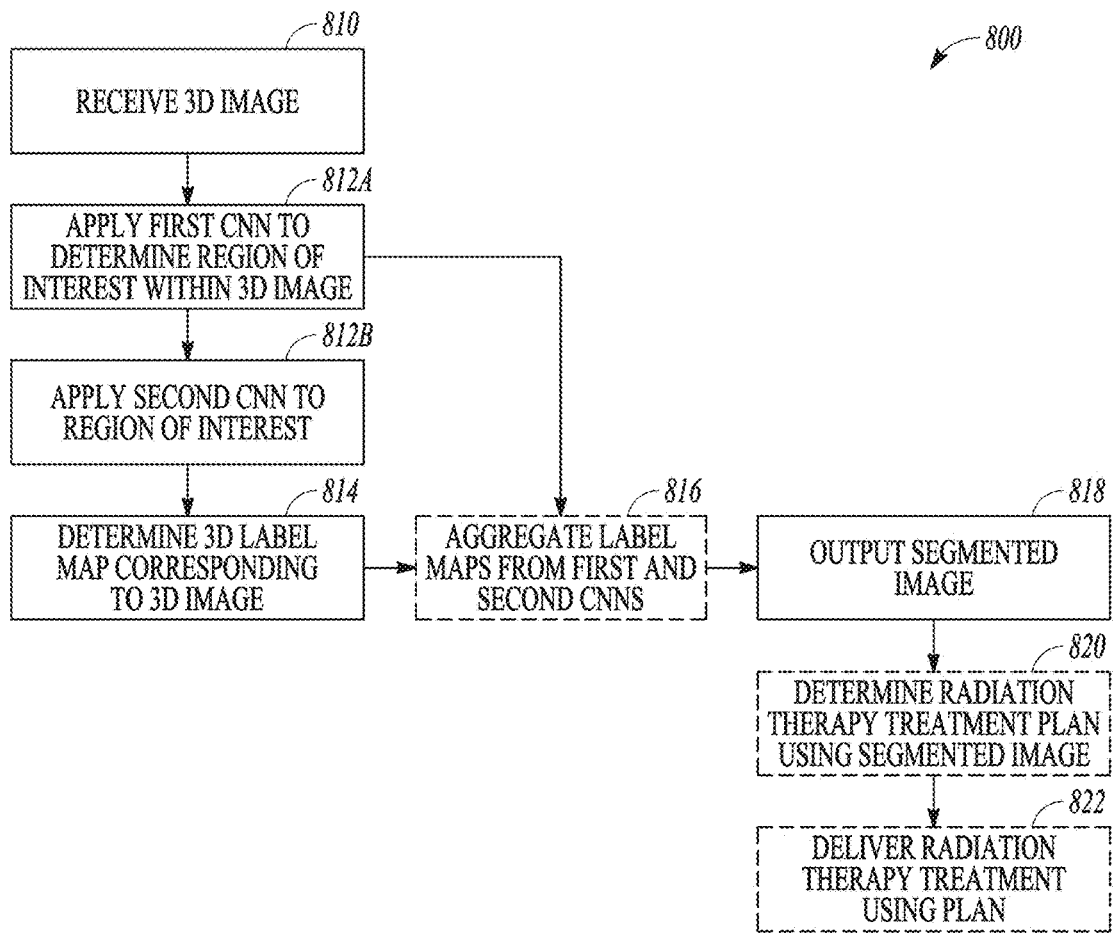
FIG. 8 illustrates generally an illustrative example of a technique, such as a method, including applying first and second convolutional neural networks (CNNs) to 3D imaging information, such as to automatically obtain a segmented image.

FIG. 8 illustrates generally an illustrative example of a technique, such as a method, including applying first and second convolutional neural networks (CNNs) to 3D imaging information, such as to automatically obtain a segmented image. At 810, information indicative of a 3D image may be received, such as corresponding to an acquired CT or MR imaging session. The 3D imaging information received at 810 may be acquired for use in radiation therapy treatment planning. At 812A a first CNN may be applied to at least a portion of the received 3D imaging information. For example, the first CNN may be a 2D or 2.5D DCNN trained to analyze the 3D imaging information by decomposing the 3D imaging information into 2D image representations. The 2D or 2.5D DCNN may provide a 2D label map or an aggregated representation of 2D label maps such as for use in determining a region of interest within the 3D imaging information. The determined region of interest may include a sub-region of the 3D for application of a second CNN at 812B. For example, if the second CNN is trained to get a more accurate segmentation of the smaller structures, such as esophagus and spinal cord, the sub-region can be automatically determined by computing the bounding box of the esophagus and spinal cord segmentation labels in the first CNN result. The second CNN may be a 3D CNN such as to determine a 3D label map of the identified region of interest at 814. In this manner, the 3D CNN is applied only to a sub-region of the original 3D image received at 810, while the first CNN may be applied to the 3D imaging information more broadly. In addition to only using the first CNN result to define a sub-region for the second CNN, we can also use the first CNN result (e.g., the aggregated 3D label map) as extra input to the second CNN. In this way, the second CNN can be trained to explicitly correct or refine the first CNN result.

Optionally, at 816, a 3D representation of a label map identified using the second CNN provided at 814 may be aggregated in the end with one or more label maps provide by the first CNN at 812A. Such an aggregated representation may be outputted as a segmented image at 818 (e.g., representing a 3D label map, or a group of 2D label maps, as illustrative examples). Optionally, at 820, a radiation therapy treatment plan may be determined at least in part using the segmented image 818 provided by application of the first and second CNNs at 812A and 812B, respectively. Optionally, at 822, a radiation therapy treatment (e.g., a specified dose or treatment fraction) may be delivered at least in part using information from the radiation therapy treatment plan provided at 820.

Generally, when applying DCNNs for 3D image segmentation, a size and shape of the model input may impact performance. Resource limitation, such as relating to GPU memory, may render it impractical to process a full 3D image in a single pass. A 2D or 2.5D model may be built that segments a 3D image slice-by-slice or a block-wise 3D model may be built to process the 3D volume in overlapping or non-overlapping blocks. Generally, a 2D (or 2.5D) model is much faster to apply, but accuracy may suffer for small or thin, elongated structures. The approach shown in FIG. 8 and mentioned elsewhere herein concerns a two-model scheme, in which trained 2.5D and 3D models may be applied in a cascaded or sequential manner, such as to segment a 3D image. As shown in FIG. 8, results from a first DCNN (e.g., a 2.5D model) are used to automatically determine a smaller region of interest (e.g., a sub-region), within which the 3D model is applied to obtain improved segmentation of small structures.

An illustrative example of an application of such a scheme may include use of a first 2.5D model for large structures such as the lungs and to get an initial segmentation of small structures such as the heart, the esophagus, and the spinal cord. An input to the 2.5D model may include 5 adjacent axial slices of size 360×360, and an output may include a 2D label (e.g., segmentation) map corresponding to the center slice of the input stack. The 2.5D model may include a structure as shown generally in the examples of FIG. 5, FIG. 6A, or FIG. 6B, for example. An accuracy of the segmentation may be limited for thin, elongated structures, such as the esophagus. For such structures, a sub-region within the original 3D input imaging data may be defined, such as using an output from the 2.5D DCNN (e.g., a feature map or label map), and a separate, 3D DCNN model may be applied to such small structures within the sub-region, such as including one or more of the heart, the esophagus, or the spinal cord, as illustrative examples.

An input to the 3D DCNN model may include a 128× 128×32 sub-volume, such as generate an output comprising a 3D segmentation map having similar or the same dimensions. An architecture of the 3D DCNN model may be similar to the examples of FIG. 5, FIG. 6A, or FIG. 6B, but may include use of 3D imaging information rather than 2D slices, and may include fewer feature channels or fewer resolution steps (e.g., fewer downsampling or corresponding upsampling layers). For example, during experimental evaluation of imaging data using the approach mentioned above, a 2.5D DCNN model such as shown in FIG. 6B may have difficulty segmenting the esophagus and sometimes the spinal cord, due to their elongated shape and small cross-section sizes. The second, 3D DCNN model was used to obtain more accurate segmentation of these two thin structures. The 3D includes a reduced number of resolution levels (e.g., from five levels to four levels). Even with such reduction, application of the second, 3D DCNN model process a full 3D input image (rather than an identified sub-region) is about five to six times slower than a "divide and conquer" approach using the 2.5D model. Accordingly, the 3D model may be selectively applied inside a defined sub-region (a region of interest) to better segment fine structures without the penalty of applying the 3D model to an entirety of the 3D input volume. Optionally, the 3D model can use the 2.5D model result as extra input beside the original imaging information.

Experimental results mentioned herein were implemented using "Caffe," a Deep Learning Framework principally developed by the Berkeley Vision and Learning Center (BVLC). Other packages can also be used, such as Tensor-Flow, MxNet, CNTK, Torch, Theano, etc. Each of the first and second DCNN models (e.g., the 2.5D model and the 3D model) were trained from scratch using a stochastic gradient descent with momentum optimization. Other optimization techniques can also be applied, such as AdaGrad, AdaDelta, RMSProp, and the Adam algorithms as available in the packages mentioned above. The initial learning rate was set to 0.001 and multiplied by 0.9 after each epoch. Each model was trained for 50 epochs. The weight decay was set to be 0.0005 and the momentum parameter set to 0.9. Data augmentation may enhance the performance of DCNN training, particularly when training data are limited. Otherwise, the model may over-fit the training data, and the model may therefore generalize poorly to new images. For the experimental results herein, training data were augmented by applying random deformations to the input images and their segmentation maps to create new training data. To accelerate training, batch normalization may also be performed after each convolutional layer to reduce internal covariant shift.

A segmentation accuracy of the two-tier DCNN technique described herein was experimentally evaluated using thoracic CT image data from three different clinics. Twelve patients were used from each clinic. Amongst the twelve patients, imaging from three patients from each clinic were designated as the test data, and the imaging data from the remaining nine patients from each clinic were collected as the training data for building the DCNN models. Training of each model took about three days using a single NVIDIA Titan X GPU with 3584 cores and 12 GB memory (available from NVIDIA. Systems, Santa Clara, Calif., U.S.A.). Applying the 2.5D model took about 0.2 seconds to generate the segmentation result for a single axial slice, and roughly 30 seconds in total for a typical 3D volume with 160 slices. Applying the 3D model to refine the esophagus and the spinal cord inside a bounding box sub-region) took another 30 seconds. Our experimental results showed that DCNN offers very accurate image segmentation with high computational speed. The experimental results described in this section involved CT imaging, but such techniques are believed generally suitable to MR images as well. MR images generally have much richer details, and well-suited for the automatic feature learning property of DCNNs. There is no requirement to manually design image features and no pre-processing is necessary. Due to large model capacity, the accuracy of a DCNN model is expected to improve as more training data is provided. Multi-channel MR images may also be used as the DCNN model input. A population-based DCNN model may also be adapted to a particular patient using training data specific to the patient, such as in view of daily images of the patient that may gradually become available over the course of radiation therapy.

Using the experimental results and apparatus mentioned above, the sequentially-applied. DCNN results agree with the ground truth well for the majority of the structures evaluated, and a difference is well within the manual contouring variation. Only the esophagus result still needs correction, as shown by average Dice values for the nine test subjects, illustrated by the experimentally-obtained values below in Table 1.

TABLE 1

Average segmentation accuracy (mean ± one standard deviation of Dice values) across nine test subjects.

|  | Left Lung | Right Lung | Heart | Esophagus | Spinal Cord |
| --- | --- | --- | --- | --- | --- |
| Dice | 0.972 ± 0.012 | 0.977 ± 0.017 | 0.920 ± 0.026 | 0.710 ± 0.084 | 0.890 ± 0.020 |

Figure 9:
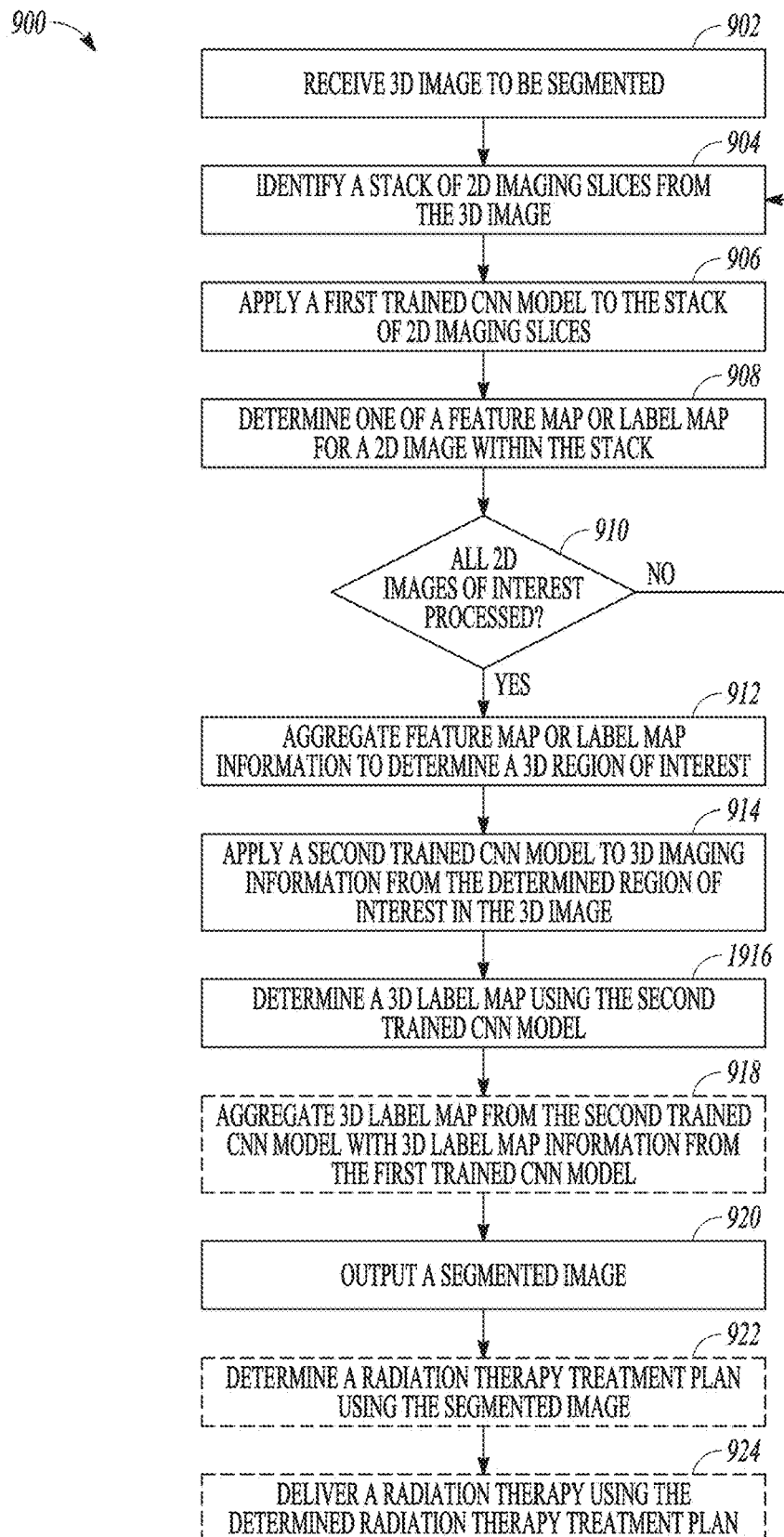
FIG. 9 illustrates generally an illustrative example of a technique, such as a method, including identifying 2D imaging slices from a 3D image for application of a first convolutional neural network (CNN), and using an output from the first CNN to determine a region of interest for application of a second CNN to 3D imaging information.

FIG. 9 illustrates generally an illustrative example 900 of technique, such as a method, including identifying 2D imaging slices from a 3D image for application of a first convolutional neural network (CNN), and using an output from the first CNN to determine a region of interest for application of a second CNN to 3D imaging information. At 902, a 3D image defining a volume may be received, for segmentation. At 904, a stack of 2D imaging slices may be identified from the 3D image. At 906, a first CNN model may be applied to the identified stack of 2D images (such as a 2.5D DCNN model as mentioned in relation to other examples). At 908, one or more of a feature map or a label map may be determined for a 2D image within the stack. At 910, if all 2D images of interest have been processed, then at 912, an aggregate feature map or label map may be generated such as for use in determination of a 3D region of interest with in the 3D input volume (e.g., a sub-region). If all 2D images of interest have not yet been processed by the first CNN, then the example 900 may identify another stack of 2D images to which the first CNN may be applied at 906. At 914, a second CNN model may be applied to the 3D region-of-interest. The second CNN model may include a 3D DCNN model that is different from the 2.5D DCNN model applied at 906. At 916, a 3D label map may be determined, at least using an output from the second trained DCNN model.

Optionally, at 918, the 3D label map from the second trained CNN model may be aggregated with information from the first CNN model. For example, if the first CNN model outputs a 3D label map formed from a series of 2D label maps, such a 3D label map may be aggregated with another 3D label from the second CNN model. In this manner, the second CNN model may provide enhanced segmentation detail for certain structures as discussed in relation to other examples. At 920, segmented imaging information may be output, such as for display or storage. For example, optionally, at 922, a radiation therapy treatment plan may be established using the segmented image. Optionally, at 924, a radiation therapy may be delivered using the radiation therapy treatment plan.

Figure 10:
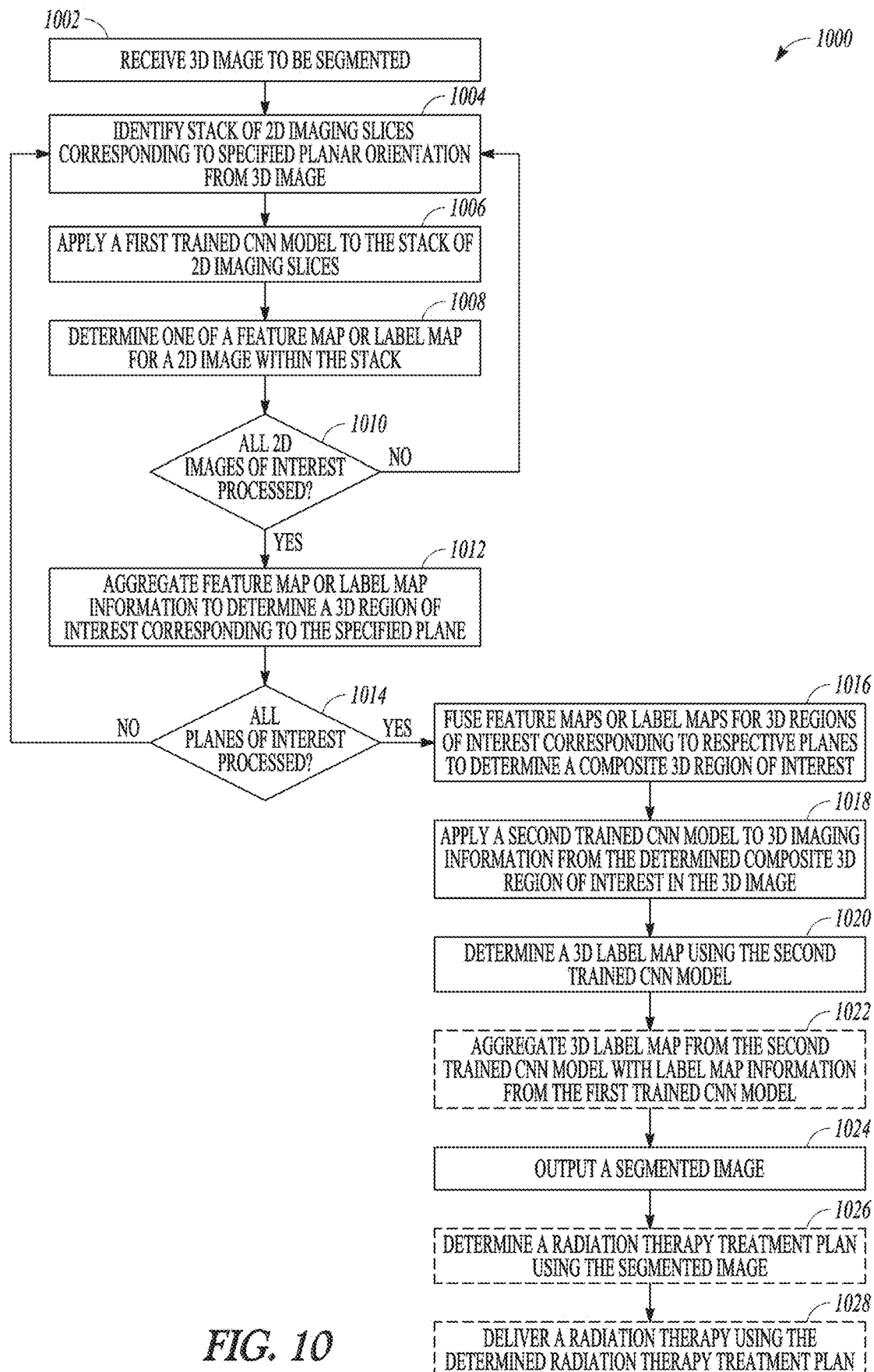
FIG. 10 illustrates generally an illustrative example of a technique, such as a method, including identifying 2D imaging slices from a 3D image for application of a first convolutional neural network (CNN), and using an output from the first CNN to determine a region of interest for application of a second CNN to 3D imaging information.

FIG. 10 illustrates generally an illustrative example 1000 of a technique, such as a method, including identifying 2D imaging slices from a 3D image for application of a first convolutional neural network (CNN), and using an output from the first CNN to determine a region of interest for application of a second CNN to 3D imaging information. At 1002, 3D imaging information may be received, such as defining a first volume. At 1004, a stack of 2D imaging slices may be identified, such as corresponding to a specified plane (e.g., axial, sagittal, or coronal), from the 3D imaging information received at 1002. At 1006, a first CNN model may be applied (e.g., a 2.5D model). At 1008 one or more of a feature map or a label map may be determined for a 2D image within the stack. At 1010, if all images of interest having a specified planar orientation have been processed, then at 1012, feature map or label map information may be aggregated, such as to determine a 3D region of interest within the volume of the 3D imaging information received at 1002. Otherwise, the example 1000 may include returning to 1004 to identify a new stack of 2D imaging slices having a specified planar orientation (e.g., orthogonal to a prior iteration), and operations 1004 through 1012 may be iterated for the new planar orientation.

At 1014, if all planar orientations of interest have been processed, then at 1016, feature map information or label map information may be fused (e.g., averaged) to determine a composite 3D region of interest (e.g., a sub-region). At 1018, a second, different CNN (e.g., a 3D DCNN) may be applied to the 3D region of interest, and at 1020 a 3D label map (e.g., a segmentation map) may be determined using the second CNN model. At 1022, optionally, an aggregate 3D label map may be established using label map information from the first DCNN (e.g., a coarse segmentation) and the 3D label map information from the second. DCNN (e.g., to provide finer segmentation within a sub-region of the originally-supplied 3D volume provided at 1002). At 1024, segmented imaging information may be output, such as for display or storage. For example, optionally, at 1026, a radiation therapy treatment plan may be established using the segmented image. Optionally, at 1028, a radiation therapy may be delivered using the radiation therapy treatment plan.

Any of the techniques discussed above may be interfaced with the radiation therapy treatment planning or therapy delivery systems mentioned elsewhere herein, or such segmentation techniques may be included as a portion of such systems.

Various Notes

Each of the non-limiting described in this document above may stand on its own, or may be combined in various permutations or combinations with one or more of the other aspects or other subject matter described in this document.

The above detailed description includes references to the accompanying drawings, which form a part of the detailed description. The drawings show, by way of illustration, specific embodiments in which the invention may be practiced. These embodiments are also referred to generally as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A computer-implemented method for segmentation of anatomical features from 3D medical imaging information, the method comprising:

receiving the three-dimensional (3D) medical imaging information defining a first volume;

applying a first trained convolutional neural network (CNN) to the three-dimensional medical imaging information to generate an initial label map for the 3D medical imaging information that associates an anatomical structure to one or more respective portions in the 3D medical imaging information;

using the initial label map generated by the first trained CNN, determining a region-of-interest within the first volume, the region-of-interest defining a lesser, second volume;

applying a different, second trained CNN to the region-of-interest to generate a refined label map corresponding to the initial label map that enhances detail about one or more anatomical structures included in the initial label map; and providing a segmented representation of the three-dimensional medical imaging information using the initial and refined label maps, wherein the second CNN provides enhanced segmentation detail in the region-of-interest without requiring application of the second CNN to an entirety of the first volume.

2. The method of claim 1, comprising displaying the segmented representation, wherein the initial label map comprises a two-dimensional (2D) label map, and wherein the refined label map comprise a 3D label map.

3. The method of claim 1, comprising determining a radiation therapy treatment plan at least in part using the segmented representation, wherein the segmented representation comprises label map information from the initial label map and label map information from the refined label map.

4. The method of claim 1, comprising:

identifying a given anatomical structure in the initial label map that is smaller than a specified size;

computing a bounding box for the given anatomical structure in the initial label map; and providing a portion of the 3D medical imaging information corresponding to the bounding box as the determined region-of-interest.

5. The method of claim 1, wherein applying the first CNN generates one or more of a feature map or label map using two-dimensional imaging information extracted from the 3D medical imaging information.

6. The method of claim 1, wherein the first CNN comprises a 2D or 2.5D deep convolutional neural network (DCNN); and wherein the second CNN comprises a 3D DCNN.

7. The method of claim 6, wherein the first CNN includes short-range and long-range connections bypassing convolutional layers included in the first CNN, the short-range connections bypassing at least one convolutional layer in an encoding portion of the first CNN, and the long connections extending between the encoding portion of the first CNN and a decoding portion of the first CNN.

8. The method of claim 1, wherein an output from the first CNN corresponding to a segmentation result within the region-of-interest is provided to the second CNN as an input along with the 3D medical imaging information, and wherein the first CNN includes at least one of a short-range or a long-range connection bypassing convolutional layers included in the first CNN.

9. The method of claim 8, comprising training at least one of the first CNN model or the second CNN model using imaging information obtained from a central repository, wherein the short-range connection bypasses at least one convolutional layer in an encoding portion of the first CNN, and wherein the long-range connection extends between the encoding portion of the first CNN and a decoding portion of the first CNN.

10. The method of claim 1, comprising training at least one of the first CNN model or the second CNN model using augmented imaging information wherein an extended set of images is generated through one or more of truncating, distorting, or scaling a first set of training images.

11. A computer-implemented method for establishing first and second convolutional neural network (CNN) models for segmentation of anatomical features from 3D medical imaging information, the method comprising:
receiving a set of training images and corresponding ground truth classification maps of anatomical features;
using the set of training images and the corresponding ground truth classification maps, determining a gradient of a first loss function and distributing information indicative of an error provided by the calculated gradient back through a first CNN model to train the first CNN model; and
using the set of training images and the corresponding classification maps, determining a gradient of a second loss function and distributing information indicative of an error provided by the calculated gradient back through a second CNN model to train the second CNN model;
wherein the second CNN provides enhanced segmentation detail as compared to the first CNN when the first and second CNNs are applied serially to the 3D medical imaging information, wherein the first CNN generates an initial label map for the 3D medical imaging information that associates an anatomical structure to one or more respective portions in the 3D medical imaging information, and wherein the second CNN generates a refined label map corresponding to the initial label map that enhances detail about one or more anatomical structures included in the initial label map.

12. The method of claim 11, wherein the first CNN comprises a 2D or 2.5D deep convolutional neural network (DCNN); and
wherein the second CNN comprises a 3D DCNN.

13. The method of claim 12, wherein the first CNN includes short-range and long-range connections bypassing convolutional layers included in the first CNN, the short-range connections bypassing at least one convolutional layer in an encoding portion of the first CNN, and the long connections extending between the encoding portion of the first CNN and a decoding portion of the first CNN.

14. The method of claim 11, wherein an output from the first CNN corresponding to a segmentation result within the region-of-interest is provided to the second CNN as an input along with the 3D medical imaging information, and wherein the first CNN includes at least one of a short-range or a long-range connection bypassing one or more convolutional layers included in the first CNN.

15. The method of claim 11, comprising training at least one of the first CNN model or the second CNN model using augmented imaging information wherein an extended set of images is generated through one or more of truncating, distorting, or scaling a received set of training images.

16. A system for segmentation of anatomical features from 3D medical imaging information, the system comprising:
processing circuitry comprising at least one processor; and
a storage medium comprising instructions, which when executed by the at least one processor, cause the processor to:
receive the three-dimensional (3D) medical imaging information defining a first volume;
apply a first trained convolutional neural network (CNN) to the three-dimensional medical imaging information to generate an initial label map for the 3D medical imaging information that associates an anatomical structure to one or more respective portions in the 3D medical imaging information;
using the initial label map generated by the first trained CNN, determine a region-of-interest within the first volume, the region-of-interest defining a lesser, second volume;
apply a different, second trained CNN to the region-of-interest to generate a refined label map corresponding to the initial label map that enhances detail about one or more anatomical structures included in the initial label map; and
provide a segmented representation of the three-dimensional medical imaging information using the initial and refined label maps, wherein the second CNN provides enhanced segmentation detail in the region-of-interest without requiring application of the second CNN to an entirety of the first volume.

17. The system of claim 16, wherein the instructions cause the processor to determine a radiation therapy treatment plan at least in part using the segmented representation, wherein the initial label map comprises a two-dimensional (2D) label map, and wherein the refined label map comprise a 3D label map.

18. The system of claim 16, wherein the instructions cause the processor to:
identify a given anatomical structure in the initial label map that is smaller than a specified size;
compute a bounding box for the given anatomical structure in the initial label map; and
provide a portion of the 3D medical imaging information corresponding to the bounding box as the determined region-of-interest.

19. The system of claim 16, wherein the instructions cause the processor to apply the first CNN to generate one or more of a feature map or label map using two-dimensional imaging information extracted from the 3D medical imaging information.

20. The system of claim 16, wherein the first CNN comprises a 2D or 2.5D deep convolutional neural network (DCNN); and
wherein the second CNN comprises a 3D DCNN.

21. The system of claim 20, wherein the first CNN includes short-range and long-range connections bypassing convolutional layers included in the first CNN, the short-range connections bypassing at least one convolutional layer in an encoding portion of the first CNN, and the long connections extending between the encoding portion of the first CNN and a decoding portion of the first CNN.

22. The system of claim 21, wherein the instructions cause the processor to provide an output from the first CNN corresponding to a segmentation result within the region-of-interest to the second CNN as an input along with the 3D medical imaging information, and wherein the first CNN includes short-range and long-range connections bypassing one or more convolutional layers included in the first CNN.

* * * * *

UNITED STATES PATENT AND TRADEMARK OFFICE
CERTIFICATE OF CORRECTION

PATENT NO. : 10,751,548 B2  
APPLICATION NO. : 15/896548  
DATED : August 25, 2020  
INVENTOR(S) : Xiao Han Page 1 of 1

It is certified that error appears in the above-identified patent and that said Letters Patent is hereby corrected as shown below:

On the Title Page

On page 2, in Column 2, item (56) under "Other Publications", Line 4, delete "Opiniont" and insert --Opinion-- therefor On page 2, in Column 2, item (56) under "Other Publications", Line 24, delete "Segmenttion"," and insert --Segmentation",-- therefor Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*